(12) United States Patent
Cui et al.

(10) Patent No.: US 7,229,825 B2
(45) Date of Patent: Jun. 12, 2007

(54) DOUBLE-TRANSFECTED CELL LINE USEFUL FOR THE IDENTIFICATION OF TRANSPORT INHIBITORS

(75) Inventors: Yunhai Cui, Heidelberg (DE); Joerg Koenig, Griesheim (DE); Dietrich Keppler, Dossenheim (DE)

(73) Assignee: Deutches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 133 days.

(21) Appl. No.: 10/729,861

(22) Filed: Dec. 5, 2003

(65) Prior Publication Data

US 2005/0003538 A1    Jan. 6, 2005

Related U.S. Application Data

(63) Continuation of application No. PCT/EP02/06175, filed on Jun. 5, 2002.

(30) Foreign Application Priority Data

Jun. 6, 2001  (EP)  .................. 01113805

(51) Int. Cl.
*C12N 5/06* (2006.01)
*C12N 5/10* (2006.01)
*C12N 15/00* (2006.01)

(52) U.S. Cl. ................ 435/325; 435/363; 435/455
(58) Field of Classification Search ...... None
See application file for complete search history.

(56) References Cited

OTHER PUBLICATIONS

Evers R, et al., Drug export activity of the human canalicular multispecific organic anion transporter in polarized kidney MDCK cells expressing cMOAT (MRP2) cDNA, 1998, J Clin Invest 101: 1310-1319.*
Konig J, et al., Conjugate export pumps of the multidrug resistance protein (MRP) family: localization, substrate specificity, and MRP2-mediated drug resistance, 1999, Biochim Biophys Acta 1461: 377-394.*
Chazot PL, et al., Molecular characterization of N-methyl-D-aspartate receptors expressed in mammalian cells yields evidence for the coexistence of three subunit types within a discrete receptor molecule, 1994, J Biol Chem 269: 24403-24409.*
Abe, T , et al., "Identification of a Novel Gene Family Encoding Human Liver-Specific Organic Anion Transporter LST-1", *Journal of Biological Chemistry*, 274(24), (Jun. 11, 1999), 17159-17163.
Acocella, G , "Clinical Pharmacokinetics of Rifampicin", *Clin Pharmacokinet*, (1978),3:108-127.
Allen, L , et al., "The Inhibition of Gammaglutamyl Transpeptidase from Human Pancreatic Carcinoma Cells by (Alpha S, 5S)-Alpha-Amino-3-Chloro-4, 5-Dihydro-5-Isoxazoleacetic Acid (AT-125; NSC-163501)", *Res Commun Chem Pathol Pharmacol*, (1980),27:175-182.

Borst, P , et al., "A Family of Drug Transporters: The Multidrug Resistance-Associated Proteins", *Natl Cancer Inst.*, 92(16), (Aug. 16, 2000), 1295-302.
Buchler, M. , et al., "cDNA cloning of the hepatocyte canalicular isoform of the multidrug resistance protein, cMrp, reveals a novel conjugate export pump deficient in hyperbilirubinemic mutant rats", *Journal of Biological Chemistry*, 271(25), (Jun. 21, 1996), 15091-15098.
Cantz, Tobias , et al., "MRP2, A Human Conguate Export Pump, is Present and Transports Fluo 3 into Apical Vacuoles of Hep G2 Cells", *Am Jour Physiol Gastrointest Liver Physiol*, (2000),278:G522-G531.
Combes, B , "The Importance of Conjugation with Glutathione for Sulfobromophthalein Sodium (BSP) Transfer from Blood to Bile", *J Clin Invest*, (1965),44:1214-1222.
Cui, Yanhai , et al., "Drug Resistance and ATP-Dependent Conjugate Transport Mediated by the Apical Multidrug Resistance Protein, MRP2, Permanently Expressed in Human and Canine Cells", *Mol Pharmacol*, (1999),55:929-937.
Cui, Yunhai , et al., "Hepatic Uptake of Bilirubin and Its Conjugates by the Human Organic Anion Transporter SLC21A6", *Journal of Biological Chemistry*, 276(13), (Mar. 30, 2001),9626-9630.
Cui, Yunhai , et al., "Vectorial Transport by Double-Transfected Cells Expressing the Human Uptake Transporter SLC21A8 and the Apical Export Pump ABCC2", Mol Pharmacol, (2001),60:934-943.
Gerloff, T , et al., "The Sister of P-Glycoprotein Represents the Canalicular Bile Salt Export Pump of Mammalian Liver", *J Biol Chem*, (1998),273:10046-10050.
Hori, R , et al., "Transport of Organic Anion in the OK Kidney Epithelial Cell Line", *Am J Physiol*, (1993),264:F975-980.
Hosoyamada, M. , et al., "Molecular Cloning and Functional Expression of a Multispecific Organic Anion Transporter from Human Kidney", *Am J Physiol*, (1999),276:F122-128.
Hsiang, Bonnie , et al., "A novel human hepatic organic anion transporting polypeptide (OATP2). Identification of a liver-specific human organic anion transporting polypeptide and identification of rat and human hydroxymethylglutaryl-CoA reductase inhibitor transporters", *Journal of Biological Chemistry*, 274(52), (Dec. 24, 1999),37161-37168.
Ishizuka, H , et al., "Species Differences in the Transport Activity for Organic Anions Across the Bile Canalicular Membrane", *J Pharmacol Exp Ther*, (1999),290:1324-1330.
Ito, K , et al., "Functional Analysis of a Canalicular Multispecific Organic Anion Transporter Cloned from Rat Liver", *J Biol Chem*, (1998),273:1684-1688.

(Continued)

*Primary Examiner*—Scott D. Priebe
*Assistant Examiner*—Michael Burkhart
(74) *Attorney, Agent, or Firm*—Schwegman, Lundberg, Woessner and Kluth P.A.

(57) ABSTRACT

Described is a double-transfected cell line containing (a) a DNA sequence encoding an uptake transporter for organic anions, preferably OATP8, operatively linked with a promoter and (b) a DNA sequence encoding an export pump for organic anions or anionic conjugates, preferably the multidrug resistance protein 2 (MRP2), operatively linked with a promoter. Moreover, various uses of said cell line are described, preferably its use for the identification of transport inhibitors, e.g. drug candidates.

10 Claims, 13 Drawing Sheets
(2 of 13 Drawing Sheet(s) Filed in Color)

OTHER PUBLICATIONS

Ito, K , et al., "Molecular Cloning of Canalicular Multispecific Organic Anion Transporter Defective in EHBR", *Am J Physicol*, (1997),272:G16-22.

Jansen, P , "Foreword: From Classic Bile Physiology to Cloned Transporters", *Semin Liver Dis 2000*, (2000),20:245-250.

Jansen, P , et al., "Selective Hepatobiliary Transport Defect for Organic Anions and Neutral Steroids in Mutant Rats with Heredity-Conjugated Hyperbilirubinema", *Hepatology*, (1987),7:71-76.

Keppler, D , et al., "Hepatic Canalicular Membrane—Intro: Transport Across the Hepatocyte Canalicular Membrane", *FASEB J*, (1997), 11:15-18.

Keppler, D , et al., "The Canalicular Conjugate Export Pump Encoded by the CMRP/CMOAT Gene", *Prog Lier Dis*, (1996),14:55-67.

Keppler, D , et al., "Transport Function and Substrate Specificity of Multidrug Resistance Protein", *Methods Enzymol*, (1998),292:607-616.

Klaassen, C , et al., "Species Variation in Metabolism, Storage and Excertion of Sulfobromophthalein", *Am J Physiol*, (1967),213:1322-1326.

Konig, J , et al., "A Novel Human Organic Anion Transporting Polypeptide Localized to the Basolateral Hepatocyte Membrane", *Am J Physiol Gastrointest Liver Physiol*, (2000),278:G156-G164.

Konig, J , et al., "Localization and Genomic Organization of a New Hepatocellular Organic Anion Transporting Polypeptide", *J Biol Chem*, (2000),275:23161-23168.

Kullak-Ublick, G , et al., "Hepatic Transport of Bile Salts", *Semin Liver Dis*, (2000),20:273-293.

Kullak-Ublick, Gerald A., et al., "Organic Anion-Transporting Polypeptide B(OATP-B) and its Funcational Comparison with Three Other OATPs of Human Liver", *Division of Chemival Pharm and Toxicology, Dept of Medicine, Univ Hospital, Zurich CH; and Institute of Anatomy, Univ of Basel, Basel, CH*, (2001), 120:525-533.

Leier, Inka , et al., "ATP-dependent para-aminohippurate transport by apical multidrug resistance protein MRP2", *Kidney International*, vol. 57,(2000), 1636-1642.

Li, L , et al., "Identification of Glutathione as a Driving Force and Leukotriene C4 as a Substrate for Oatpl, the Hepatic Sinusoidal Organic Solute Transporter", *J Biol Chem*, (1998),273:16184-16191.

Madon, J , et al., "Functional Expression of the Rat Liver Canalicular Isoform of the Multidrug Resistance-Associated Protein", *FEBS Lett*, (1997),406:75-78.

Minta, A , et al., "Fluorescent Indicators for Cytosolic Calcium Based on Rhodamine and Fluorescein Chromopores", *J Biol Chem*, (1989),264:8171-8178.

Nies, A , et al., "Expression of the Apical Conjugate Export Pump, Mrp2, in the Polarized Hepatoma Cell Line, WIF-B", *Hepatology*, (1998),28:1332-1340.

Paulusma, C , et al., "Congenital Jaundice in Rats with a Mutation in a Multidrug Resistance-Associated Protein Gene", *Science*, (1996),271:1126-1128.

Sambrook, "Molecular Cloning", *A Laboratory Manual*, Cold Spring Harbor Laboratory,(2001).

Scharschmidt, B , et al., "Hepatic Organic Anion Uptake in the Rat", *J Clin Invest*, (1975),56:1280-1292.

Schaub, T , et al., "Expression of the MRP2 Gene-Encoded Conjugate Export Pump in Human Kidney Proximal Tubules and in Renal Cell Carcinoma", *J Am Soc Nephrol*, (1999), 10:1159-1169.

Snel, C , et al., "Glutathione Conjugation of Bromosulfophthalein in Relation to Hepatic Glutathione Content in the Rat in Vivo and in the Perfused Rat Liver", *Hepatology*, (1995),21:1387-1394.

Strautnieks, S , et al., "A Gene Encoding A Liver-Specific ABC Transporter is Mutated in Progressive Familial Intrahepatic Cholestasis", *Nat Genet*, (1998),20:233-238.

Suzuki, H , et al., "Excretion of GSSG and Glutathione Conjugates Mediated by MRP1 and cMOAT/MRP2", *Semin Liver Dis*, (1998), 18:35-376.

Terasaki, M , et al., "Localization of Endoplasmic Reticulum in Living and Glutaraldehyde-Fixed Cells with Fluorescent Dyes", *Cell*, (1984),38:101-108.

Tojo, A , et al., "Immunohistochemical Localization of Multispecific Renal Organic Anion Transporter 1 in Rat Kidney", *J Am Soc Nephrol*, (1999),10:464-471.

Wang, R , et al., "Targeted Inactivation of Sister of P-Glycoprotein Gene (SPGP) in Mice Results in Nonprogressive but Persistent Intrahepatic Cholestasis", *Proc Natl Acad Sci USA*, (2001),98:2011-2016.

Whelan, G , et al., "A Direct Assessment of the Importance of Conjugation for Biliary Transport of Sulfobromophthalein Sodium", *J Lab and Clin Med*, (1970),75:542-557.

* cited by examiner

DOUBLE-TRANSFECTED CELL LINE USEFUL FOR THE IDENTIFICATION OF TRANSPORT INHIBITORS

RELATED APPLICATIONS

This application is a continuation under 35 U.S.C. 111(a) of International Application No. PCT/EP02/06175 filed Jun. 5, 2002 and published in English as WO 02/099088 A1 on Dec. 12, 2002, which claimed priority from European Application No. EP 01113805.4 filed Jun. 6, 2001, which applications and publication are incorporated herein by reference.

The present invention relates to a double-transfected cell line containing (a) a DNA sequence encoding an uptake transporter for organic anions, preferably OATP8, operatively linked with a promoter and (b) a DNA sequence encoding an export pump for organic anions or anionic conjugates, preferably the multidrug resistance protein 2 (MRP2), operatively linked with a promoter. The present invention also relates to various uses of said cell line, preferably for the identification of transport inhibitors, e.g. drug candidates.

Vectorial transport is an important function of all polarized cells contributing to detoxification and to the prevention of entry of toxins into organs. This is exemplified by kidney proximal tubule epithelia, by cells of the blood-brain barrier, by intestinal epithelia, and, last but not least, by hepatocytes. One of the major hepatocellular functions is the removal of endogenous and exogenous substances from the blood circulation and their secretion into the bile. Two transport processes play a decisive role in this vectorial transport by hepatocytes: the sinusoidal (basolateral) uptake from blood and the canalicular (apical) secretion into bile. In human hepatocytes, the sodium-independent uptake of amphiphilic organic anions is mediated by at least three transport proteins, namely by the human organic anion transporters OATP2 (also known as OATP-C or LST1, symbol SLC21A6) (Abe et al. 1999; Hsiang et al. 1999; König et al. 2000a; Cui et al. 2001), human OATP8 (SLC21A8) (König et al. 2000b; Cui et al. 2001), and human OATP-B (SLC21A9) (Kullak-Ublick et al. 2001). All three transporters belong to the subgroup 21A of the solute carrier (SLC) superfamily. Whereas OATP-B is expressed also in a number of other tissues, OATP2 and OATP8 are expressed exclusively in human hepatocytes. The substrate spectrum of OATPs includes bile salts, conjugates of steroid hormones, thyroid hormones, and many other amphiphilic organic anions (Abe et al. 1999; König et al. 2000a, b; Cui et al. 2001; Kullak-Ublick et al. 2000, 2001). Unlike these basolateral uptake transporters which are thought to be of exchanger type (Li et al. 1998), the apical export transporters identified in human hepatocytes so far are members of the ATP-binding cassette (ABC) superfamily (Keppler and Arias 1997; Jansen 2000). The export of organic anions is predominantly mediated by the bile salt export pump BSEP (ABCB11) belonging to the MDR (ABCB) subgroup of the ABC superfamily (Strautnieks et al. 1998; Gerloff et al. 1998; Wang et al. 2001) and by the multidrug resistance protein 2 (MRP2, ABCC2) belonging to the MRP (ABCC) subgroup of the ABC superfamily (Buchler et al. 1996; Suzuki and Sugiyama 1998; König et al. 1999; Borst et al. 2000). While the major substrates of BSEP are bile salts like cholyl taurine and cholate (Gerloff et al. 1998), the organic anions transported by MRP2 are mainly conjugates of lipophilic substances with glutathione, glucuronate, or sulfate (Evers et al. 1998; Cui et al. 1999, König et al. 1999).

The transhepatic transport of amphiphilic organic anions has been frequently studied by use of model compounds like sulfobromophthalein (BSP) and indocyanine green (ICG) (Scharschmidt et al. 1975). Functional characterization of the three human OATPs identified in the hepatocyte basolateral membrane demonstrated that all three are able to mediate the uptake of BSP, with the highest affinity for OATP2 ($K_m$=140 nM) and the lowest affinity ($K_m$=3.4 μM) for OATP8 (König et al. 2000b; Kullak-Ublick et al. 2001; Cui et al. 2001). In the hepatocyte BSP is predominantly conjugated with glutathione to yield the BSP glutathione S-conjugate (BSP-SG) (Whelan et al. 1970; Snel et al. 1995). Studies with transport-deficient mutant rats (Jansen et al. 1987) which lack the canalicular export pump Mrp2 (Paulusma et al. 1996; Büchler et al. 1996; Ito et al. 1997) suggested that this export pump mediates the secretion of BSP-SG into bile. However, it was not established that BSP itself is a substrate for human MRP2. So far, the transport proteins like OATPs and MRPs were studied mostly by use of transfected mammalian cells or by use of Xenopus oocyte systems expressing only one exogenous recombinant transport protein (Madon et al. 1997; Ito et al. 1998; Evers et al. 1998; Cui et al. 1999, 2001; Abe et al. 1999; Hsiang et al. 1999; König et al. 2000a, b; Kullak-Ublick et al. 2001).

When developing or designing new pharmaceuticals one of the critical questions is to whether the candidate compounds have undesired side effects like interference with the transport of substances which are produced or occur naturally in the body, e.g. interference with the hepatic or renal transport of organic anions, as exemplified by the interference of rifampicin, rifamycin SV, or CDNB with the transcellular transport of BSP. For cost saving, it is desirable to detect such side effects of drug candidates at an early stage of development. So far, for the study of potential side effects of drug candidates animals or cell cultures were used. However these approaches exhibit a variety of disadvantages, e.g. are time and cost consuming, do not allow the high throughput screening of drug candidates etc.

Therefore, it is the object of the present invention to provide a means for the efficient analysis of the interference of a drug candidate with transport of substances which are produced or occur naturally in the body, particularly interference with the hepatic or renal transport of organic anions which overcomes the disadvantages of the systems presently used.

According to the invention this is achieved by the subject matters defined in the claims. A cell system with defined human uptake and export transporters was established, i.e. a double-transfected MDCK cell line permanently expressing a recombinant uptake transporter for organic anions in the basolateral membrane and an ATP-dependent export pump for anionic conjugates in the apical membrane. Basolateral uptake was mediated by the human organic anion transporter OATP8 (symbol SLC21A8) and subsequent apical export by the multidrug resistance protein 2 (MRP2; symbol ABCC2). Under physiological conditions, both transport proteins are strongly expressed in hepatocytes and contribute to the hepatobiliary elimination of organic anions. Expression and localization of OATP8 and MRP2 in MDCK cells growing on Transwell membrane inserts was demonstrated by immunoblotting and confocal laser scanning microscopy. $^3$H-Labeled sulfobromophthalein (BSP) was a substrate for both transport proteins and was transferred from the basolateral to the apical compartment at a rate at least 6 times faster by double-transfected MDCK-MRP2/OATP8 cells than by single-transfected MDCK-OATP8 or MDCK-MRP2 cells. Vectorial transport at a much higher rate by double-transfected than by single-transfected cells was also observed for the $^3$H-labeled substrates leukotriene C$_4$, 17b-glucuronosyl estradiol, and dehydroepiandrosterone sulfate, for the fluorescent anionic substrate fluo-3, and for the antibiotic rifampicin. Inhibition studies indicated that intracellular formation of S-(2,4-dinitrophenyl)-glutathione from 2,4-chlorodinitrobenzene selectively inhibits the transcellular transport of [$^3$H]BSP at the site of MRP2-mediated export.

The identification of the new substrates for MRP2 and OATP8 demonstrates that the double-transfected cell line is useful for the characterization of these transporters. In comparison to MDCK cells transfected separately with either OATP8 or MRP2, the double-transfectants have several advantages. It was so far difficult to study MRP2 function in whole cells because most substrates for MRP2 are negatively charged under physiological conditions and thus can not penetrate the plasma membrane without an uptake transporter. Therefore, MRP2 has been mostly studied using inside-out membrane vesicles prepared from MRP2-expressing cells. With the double-transfected MDCK cells expressing OATP8 and MRP2 and with compounds like [$^3$H]BSP and Fluo-3, which are substrates for both transporters, we may now screen more easily for MRP2 inhibitors with intact cells. An inhibitor for only MRP2 will inhibit the transcellular transport and enhance the intracellular accumulation of [$^3$H]BSP. An inhibitor for both MRP2 and OATP8 will reduce the transcellular transport more strongly than the intracellular accumulation of [$^3$H]BSP. Because of the easier handling of double-transfected cells grown on Transwell membrane inserts in comparison with the preparation and handling of membrane vesicles, it is possible to develop high-throughput screening systems for MRP2 inhibitors by the use of the double-transfected cells. The use of the fluorescent penta-anion Fluo-3 as a substrate for both OATP8 and MRP2 may further facilitate the screening.

To conclude, the double-transfected cells of the present invention provide a useful system for the identification of transport substrates and transport inhibitors including drug candidates. By using the double-transfected cell line of the present invention the inhibiting effect of drug candidates on defined transport proteins which are, e.g., present in liver, kidney, intestine or blood brain barrier can be investigated.

Accordingly, the present invention provides a double-transfected cell line, preferably a stable cell line containing (a) a DNA sequence encoding an uptake transporter for organic anions operatively linked with a promoter and (b) a DNA sequence encoding an export pump for organic anions or anionic conjugates operatively linked with a promoter. Preferably, the uptake transporter for organic anions is expressed in the basolateral cell membrane and the export pump for organic anions or anionic conjugates is expressed in the apical cell membran.

Preferably, for transfecting the cells the DNA sequences are present in a vector or expression vector. A person skilled in the art is familiar with examples thereof. The DNA sequences can also be contained in a recombinant virus containing appropriate expression cassettes. Suitable viruses that may be used in the present invention include baculovirus, vaccinia, sindbis virus, SV40, Sendai virus, adenovirus, an AAV virus or a parvovirus, such as MVM or H-1. The vector may also be a retrovirus, such as MoMULV, MoMuLV, HaMuSV, MuMTV, RSV or GaLV. For expression in mammals, a preferred suitable promoter is human cytomegalovirus "immediate early promoter" (pCMV).

For generating the above described DNA sequences and for constructing expression vectors which contain said DNA sequences, it is possible to use general methods known in the art. These methods include e.g. in vitro recombination techniques, synthetic methods and in vivo recombination methods as described in Sambrook et al., Molecular Cloning, A Laboratory Manual, $2^{nd}$ edition (1989) Cold Spring Harbor Laboratory Press, Cold Spring Harbor, N.Y., for example. Methods of transfecting the cells, of phenotypically selecting transfectants and of expressing the DNA according to the invention by using the above described vectors are known in the art.

Preferably, the cell line is a human cell line, e.g. HEK293. Particularly preferred are polarized cells, e.g. hepatocytes, kidney cells, e.g. MDCKII or HepG2.

In a further preferred embodiment of the double-transfected cell line of the present invention the uptake transporter for organic anions is a member of the subgroup 21A of the solute carrier (SLC) superfamily. Particularly preferred are OAT1 (SLC22A6) (Hosoyamada et al. 1999), OATP2, OATP8 or OATP-B.

In a more preferred embodiment of the double-transfected cell line of the present invention the export pump for organic anions or anionic conjugates is a member of the MDR (ABCB) subgroup or the MRP (ABCC) subgroup of the ABC superfamily. Particularly preferred are the bile salt export pump BSEP (ABCB11) or the multidrug resistance protein 2 (MRP2). A combination of OAT1 with MRP2, both of which are expressed in human kiodney proximal tubule cells (Tojo et al. 1999; Schaub et al. 1999), may serve to study the renal clearance of organic anions.

In an even more preferred of the double-transfected cell line of the present invention the DNA sequence encoding an uptake transporter for organic anions and/or the DNA sequence encoding an export pump for organic anions or anionic conjugates are operatively linked with a promoter allowing high expression.

In certain cases for investigating the effect of the intracellular drug metabolism on transport it might be desirable to transfect the cells of the invention with a DNA sequence encoding a third compound the nature of which may vary according to the drug to be studied.

Finally, the present invention relates to various uses of the double-transfected cell line. A preferred use is the identification of a transport substrate or a transport inhibitor, particularly a drug candidate. Suitable assays formats are known to the person skilled and, e.g., described in the examples, below. A preferred assay format is high throughput screening.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A–1B. Immunoblot analysis of MRP2 and OATP8 in transfected MDCK cells. Crude membrane fractions from MDCK cells permanently transfected with control vector (MDCK-Co), with human MRP2 (MDCK-MRP2), with human OATP8 (MDCK-OATP8), or with both MRP2 and OATP8 cDNA (MDCK-MRP2/OAT8) were separated by SDS-PAGE. A, Human MRP2 was detected by the polyclonal antibody EAG5 (Keppler and Kartenbeck 1996; Schaub et al., 1999). B, Human OATP8 was detected by the polyclonal antibody SKT (König et al. 2000b). In case of OATP8, only the fully glycosylated form is indicated by an arrowhead, whereas the band is about 90 kDa represents under-glycosylated form of the protein (König et al. 2000b).

FIG. 2A–2F. Immunolocalization of recombinant MRP2 and OATP8 in MDCK cells. MDCK cells expressing OATP8 alone (A, D) or both MRP2 and OATP8 (B, C, E, and F) were grown on Transwell membrane inserts and examined by confocal laser scanning microscopy. OATP8 (green fluorescence) and MRP2 (red fluorescence) were stained using the polyclonal antibody SKT (König et al. 2000b) and the monoclonal antibody $M_2III6$ (Evers et al. 1998), respectively. A and B are en face images focused at the middle of the cell monolayer, C is an en face image focused at the top of the cell monolayer. D, E, and F are vertical sections at the positions indicated by the white lines in A, B, and C. Besides the lateral localization of OATP8, some intracellular staining of this protein can be seen in the vertical sections. Only MRP2 is localized to the apical membrane (E, F). Bar, 10 μm.

FIG. 4A–4B. Transcellular transport of [$^3$H]BSP. MDCK-Co (Δ), MDCK-MRP2 (▲), MDCK-OATP8 (□), and MDCK-MRP2/OATP8 (■) cells were grown on Transwell membrane inserts. [$^3$H]BSP (1 μM) was given to the basolateral compartments. At the time points indicated, radioactivity in the apical compartments (Transcellular [$^3$H]BSP transport) and inside the cells (Transcellular [$^3$H]BSP accumulation) was determined. Total uptake of [3H]BSP was calculated as the sum of intracellular and apical radioactivity. Data represent means±SD (n=4). For most measurements the standard deviation was within the size of the symbols.

FIG. 5A–5B. Vectorial transport and efflux of [$^3$H]BSP. MDCK-OATP8 and MDCK-MRP2/OATP8 cells were grown on Transwell membrane inserts. A, Vectorial transport of [$^3$H]BSP. [$^3$H]BSP (1 μM) was given either to the basolateral compartments (B→A) or to the apical compartments (A→B). After 15 min at 37° C., radioactivity in the opposite compartments was measured. B, Efflux of [$^3$H]BSP. MDCK-OATP8 and MDCK-MRP2/OATP8 cells were incubated with [$^3$H]BSP (1 μM) in the basolateral compartments at 37° C. for 30 min. The cells were then washed with cold buffer and incubated with buffer without [$^3$H]BSP at 37° C. for 30 min. The radioactivity subsequently released into the basolateral and the apical compartment and inside the cells was measured. Data represent means±SD (n=4).

FIG. 6A–6C. HPLC analyses of [$^3$H]BSP. MDCK-MRP2/OATP8 cells grown on Transwell membrane inserts were incubated with 1 μM [$^3$H]BSP in the basolateral compartment at 37° C. for 30 min. The medium in the apical compartment and the cell lysate were analyzed by radio-HPLC as described in "Materials and Methods". A, Authentic [$^3$H]BSP (Cui et al. 2001); B, radioactivity collected in the apical compartment; C, radioactivity accumulated in the cells. [$^3$H]BSP (arrow head) and the glutathione S-conjugate of [$^3$H]BSP ([$^3$H]BSP-SG, arrow) are indicated. Acivicin, an inhibitor of the degradation of the glutathione moiety of [$^3$H]BPS-SG, was added to the incubation at a concentration of 5 mM.

FIG. 7A–7C. ATP-dependent transport of [$^3$H]BSP by human MRP2. A, Inside-out membrane vesicles from HEK293 cells transfected with human MRP2 (HEK-MRP2) were incubated with 1 μM [$^3$H]BSP in the presence of ATP (■) or 5'-AMP (□). B, Net ATP-dependent transport of

[³H]BSP into the vesicles from HEK-MRP2 cells (■) or HEK-Co cells (□) was calculated by subtracting the values determined in the presence of 5'-AMP from those in the presence of ATP. C, The $K_m$ value of human MRP2 for BSP was determined at BSP concentrations between 1 and 10 µM. Data represent means±SD (n=4).

Figure 7:
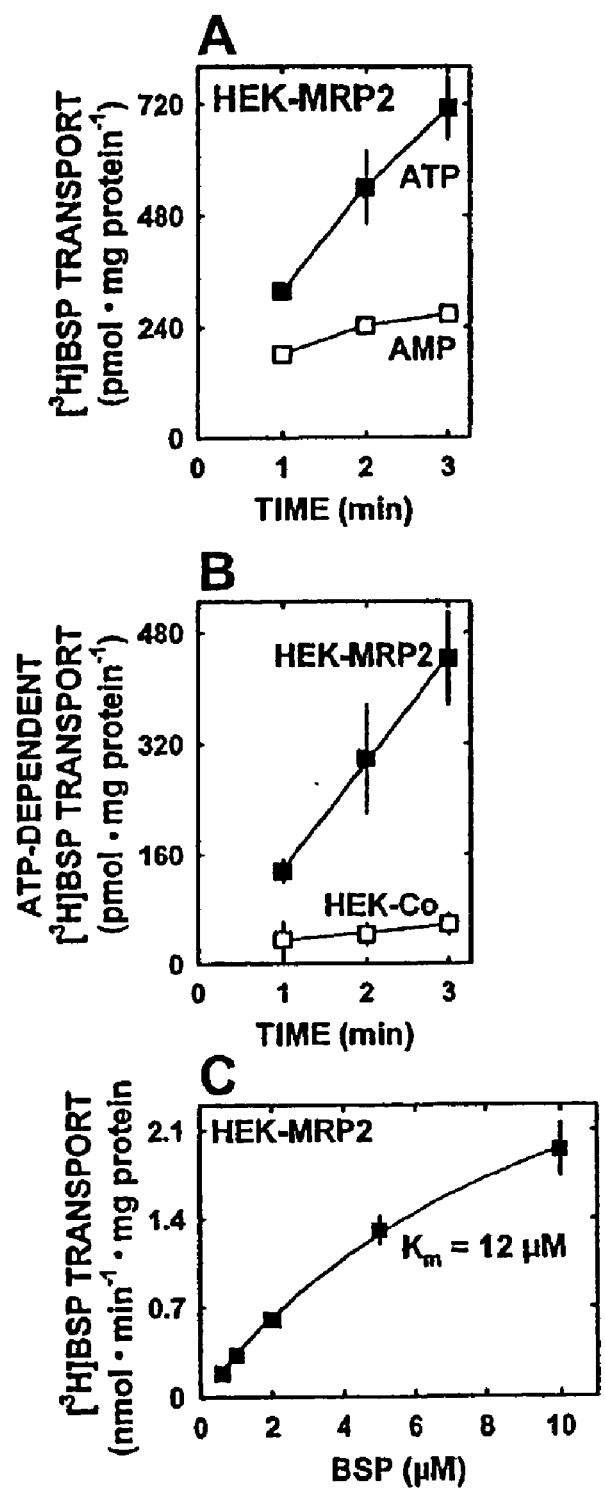

FIG. 7. ATP-dependent transport of [³H]BSP by human MRP2. A, Inside-out membrane vesicles from HEK293 cells transfected with human MRP2 (HEK-MRP2) were incubated with 1 µM [³H]BSP in the presence of ATP (g) or 5'-AMP (c). B, Net ATP-dependent transport of [³H]BSP into the vesicles from HEK-MRP2 cells (g) or HEK-Co cells (c) was calculated by subtracting the values determined in the presence of 5'-AMP from those in the presence of ATP. C, The $K_m$ value of human MRP2 for BSP was determined at BSP concentrations between 1 and 10 µM. Data represent means±SD (n=4).

FIG. 8A–8F. Transcellular transport of organic anions. MDCK-Co, MDCK-OATP8, and MDCK-MRP2/OATP8 cells grown on Transwell membrane inserts were incubated with [³H]BSP (1 µM), [³H]LTC$_4$ (0.5 µM), [³H]E$_2$17bG (5 µM), [³H]DHEAS (5 µM), Fluo-3 (2 µM) or [³H]cholyl taurine (5 µM) in the basolateral compartments at 37° C. The radioactivity (labeled substrates) or fluorescence (Fluo-3) in the apical compartments was then measured after 30 min. Data represent means±SD (n=4).

Figure 8:
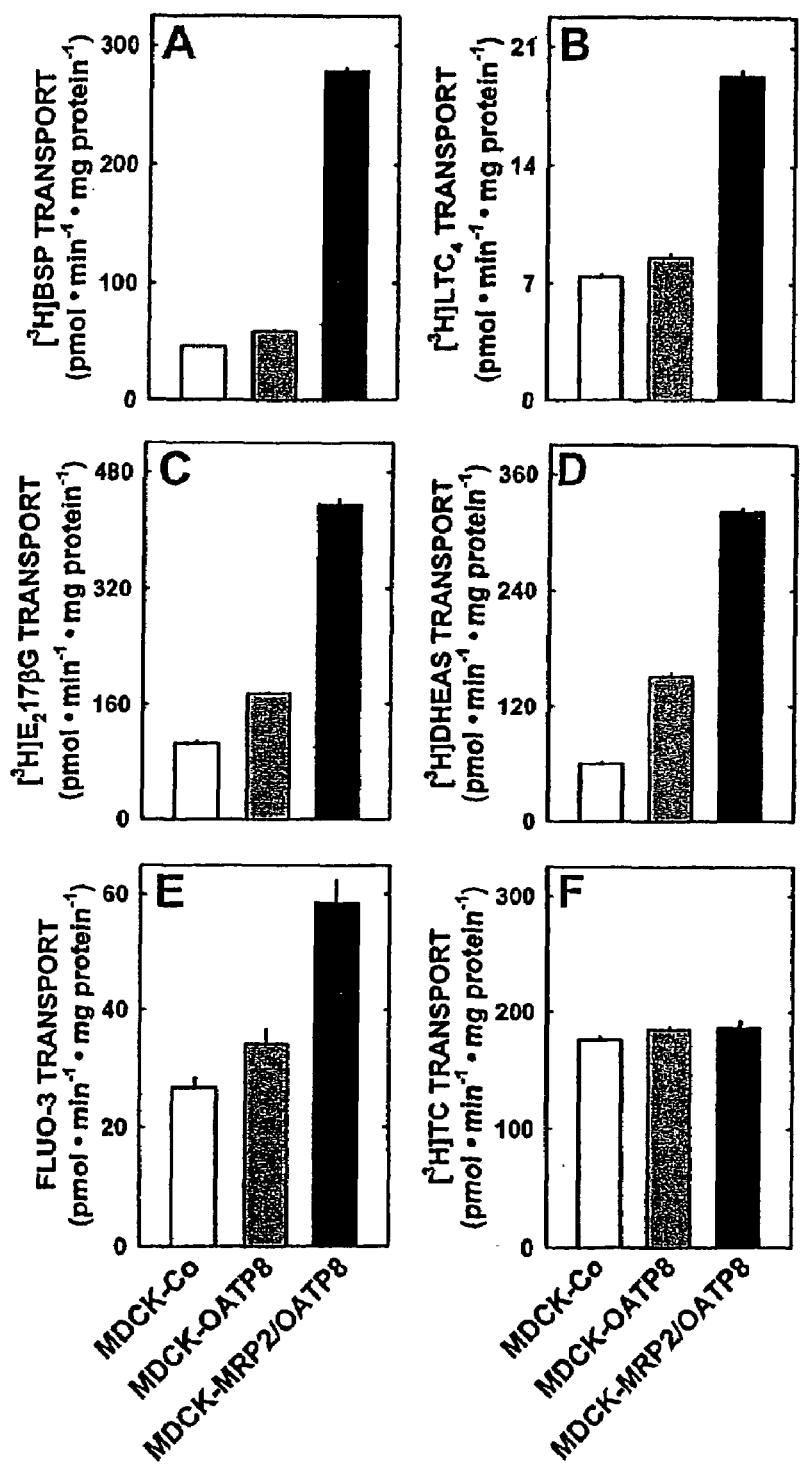

FIG. 8. Transcellular transport of organic anions. MDCK-Co, MDCK-OATP8, and MDCK-MRP2/OATP8 cells grown on Transwell membrane inserts were incubated with [³H]BSP (1 µM), [³H]LTC$_4$ (0.5 µM), [³H]E$_2$17bG (5 µM), [³H]DHEAS (5 µM), Fluo-3 (2 µM) or [³H]cholyl taurine (5 µM) in the basolateral compartments at 37° C. The radioactivity (labeled substrates) or fluorescence (Fluo-3) in the apical compartments was then measured after 30 min. Data represent means±SD (n=4).

FIG. 9A–9H. Inhibition of the transcellular transport of [³H]BSP. MDCK-OATP8 (A, C, B, G), and MDCK-MRP2/OATP8 (B, D, F, H) cells grown on Transwell membrane inserts were incubated with [³H]BSP (1 µM) in the basolateral compartments in the presence of different concentrations of human serum albumin (HSA, C, D), rifampicin (E, F), or rifamycin SV (G, H). For 2,4-chloro-dinitrobenzene (CDNB) (A, B), cells were pre-incubated with CDNB at room temperature for 20 min, transport of [³H]BSP was started by replacing the buffer in the basolateral compartments by fresh buffer containing [³H]BSP and CDNB. After incubation for 30 min at 37° C., the radioactivity in the apical compartments and inside the cells was measured. Data represent means ±SD(n=4).

Figure 9:
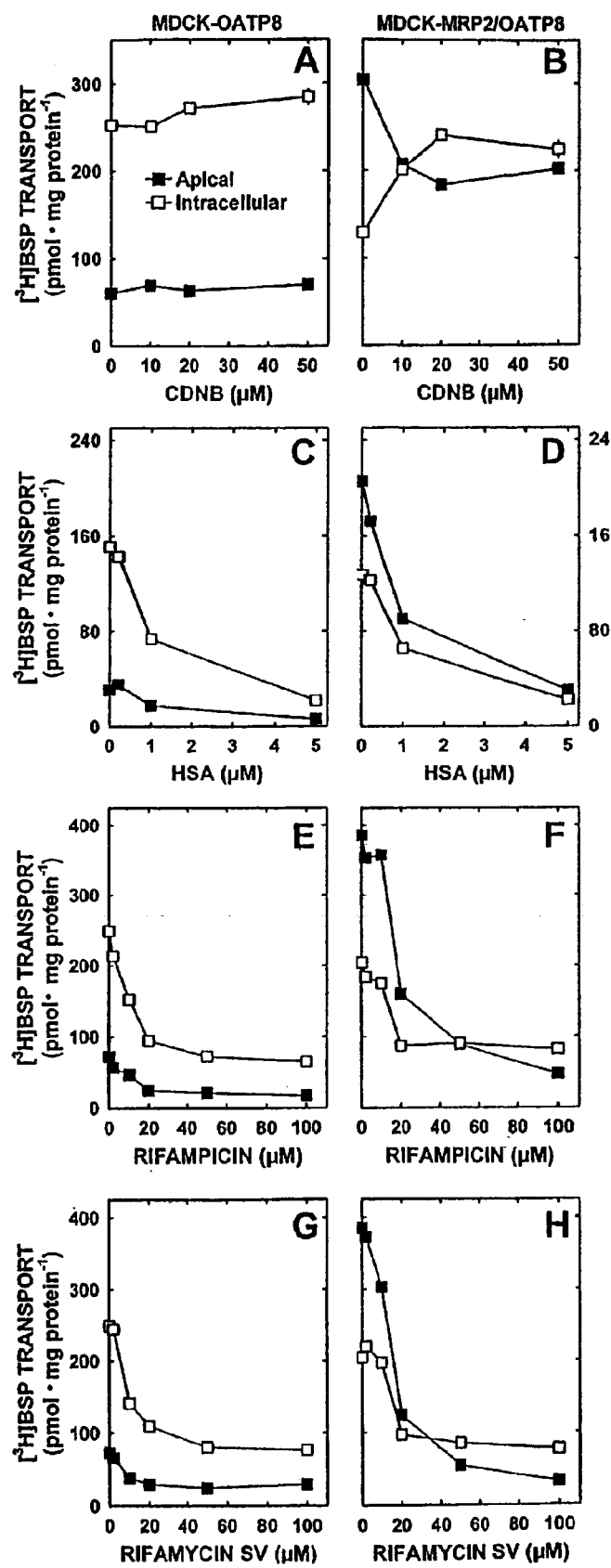

FIG. 9. Inhibition of the transcellular transport of [³H] BSP. MDCK-OATP8 (A, C, E, G), and MDCK-MRP2/OATP8 (B, D, F, H) cells grown on Transwell membrane inserts were incubated with [³H]BSP (1 µM) in the basolateral compartments in the presence of different concentrations of human serum albumin (HSA, C, D), rifampicin (E, F), or rifamycin SV (G, H). For 2,4-chloro-dinitrobenzene (CDNB) (A, B), cells were pre-incubated with CDNB at room temperature for 20 min, transport of [³H]BSP was started by replacing the buffer in the basolateral compartments by fresh buffer containing [³H]BSP and CDNB. After incubation for 30 min at 37° C., the radioactivity in the apical compartments and inside the cells was measured. Data represent means±SD (n=4).

Figure 10:
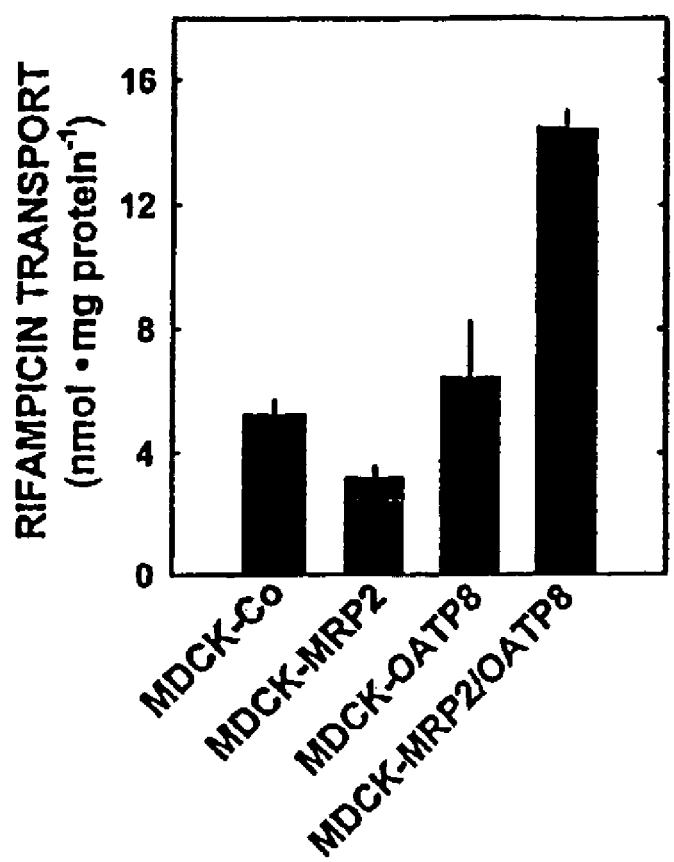

FIG. 10. Transcellular transport of rifampicin. MDCK-Co, MDCK-MRP2, MDCK-OATP8, and MDCK-MRP2/OATP8 cells grown on Transwell membrane inserts were incubated with 50 µM rifampicin in the basolateral compartments at 37° C. for 30 min. The concentration of rifampicin in the apical compartments was determined by the specific absorption of rifampicin at 475 nm. Data represent means±SD (n=4).

FIG. 11A–11D: Immunolocalisation of recombinant transport proteins in double-transfected cell lines. MDCKII cells transfected with OAT1 and MRP2 (A, C) or with OATP2 and MRP2 (B, D) were grown on Transwell membrane inserts. Recombinant MRP2 was stained with the antiserum EAG5 (green in A, C) or with the commercial antibody M$_2$III6 (red in B, D). Recombinant OAT1 was stained with a commercial monoclonal antibody against an epitope at the carboxyl terminus of OAT1 (red in A, C). Recombinant OATP2 was stained with the polyclonal antiserum ESL (green in B, D). In both double-transfected cell lines, MRP2 was localized to the apical membrane of polarized MDCKII cells. OAT1 and OATP2 were detected only in the basolateral membrane of the respective cell lines.

Figure 11:
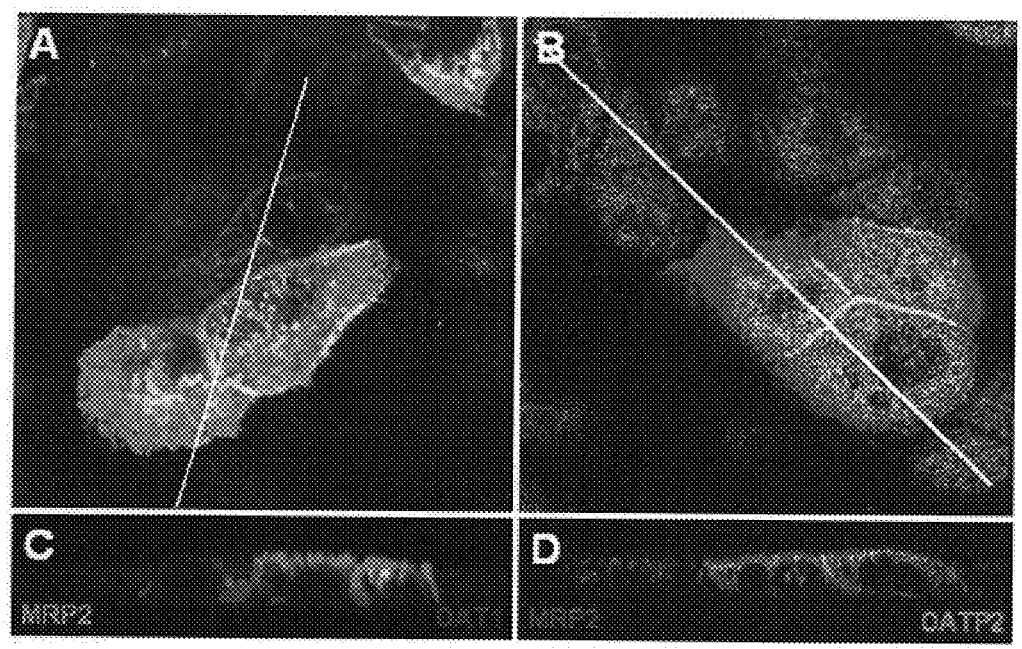

FIG. 11: Immunolocalisation of recombinant transport proteins in double-transfected cell lines. MDCKII cells transfected with OAT1 and MRP2 (A,C) or with OATP2 and MRP2 (B,D) were grown on Transwell membrane inserts. Recombinant MRP2 was stained with the antiserum EAG5 (green in A,C) or with the commercial antibody M$_2$III6 (red in B, D). Recombinant OAT1 was stained with a commercial monoclonal antibody against an epitope at the carboxyl terminus of OAT1 (red in A, C). Recombinant OATP2 was stained with the polyclonal antiserum ESL (green in B, D). In both double-transfected cell lines, MRP2 was localized to the apical membrane of polarized MDCKII cells. OAT1 and OATP2 were detected only in the basolateral membrane of the respective cell lines.

Figure 12:
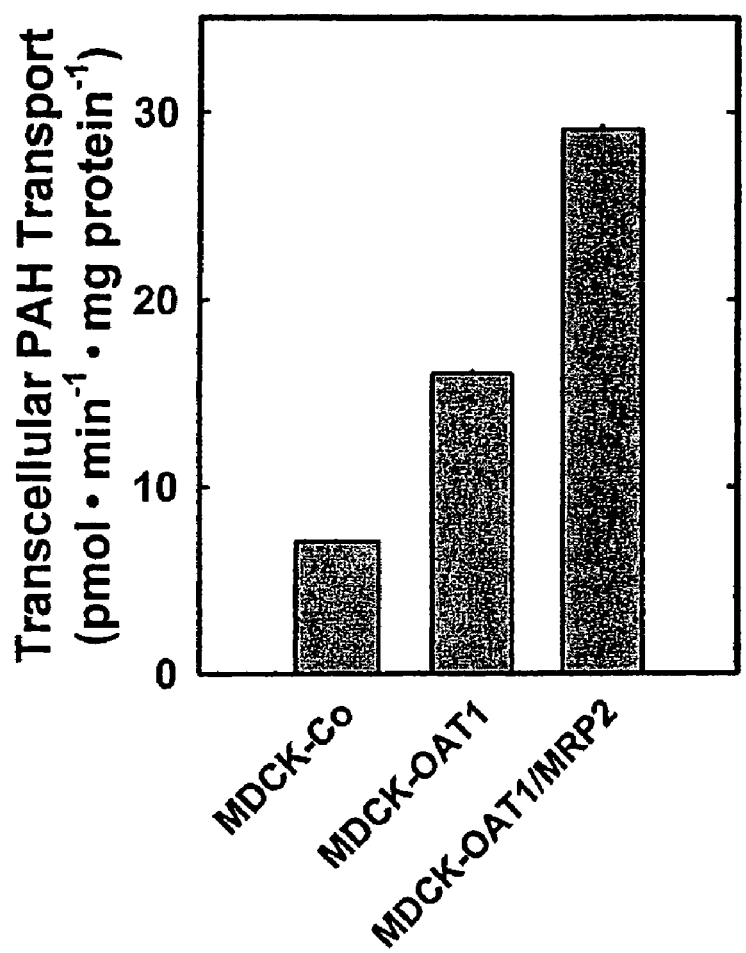

FIG. 12: Transcellular transport of para-aminohippurate (PAH) by MDCK-OAT1/MRP2 cells. MDCKII cells transfected with control vector (MDCK-Co), with OAT1 (MDCK-OAT1), or with both OAT1 and MRP2 (MDCK-OAT1/MRP2) were grown on Transwell membrane inserts and incubated with 10 µM [³H]PAH added to the basolateral compartment at 37° C. Radioactivity accumulated in the apical compartment was measured after 30 min.

Figure 13:
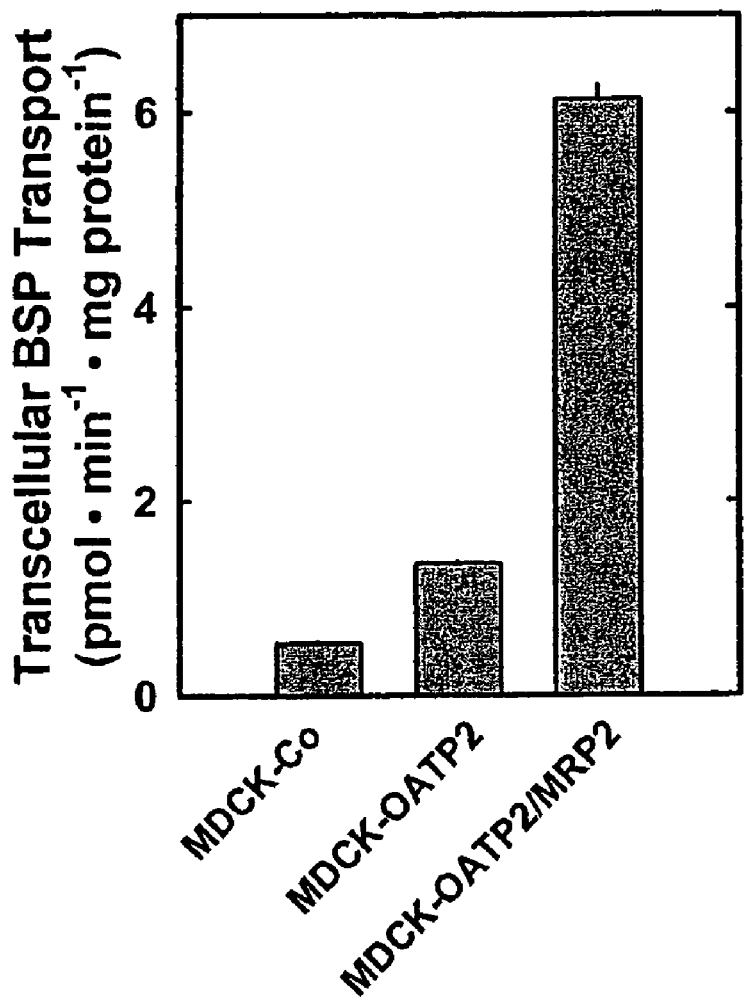

FIG. 13: Transcellular transport of BSP by MDCK-OATP2/MRP2 cells. MDCKII cells transfected with control vector (MDCK-Co), with OATP2 (MDCK-OATP2), or with both OATP2 and MRP2 (MDCK-OATP2/MRP2) were grown on Transwell membrane inserts and incubated with 1 µM [³H]BSP added to the basolateral compartment at 37° C. Radioactivity accumulated in the apical compartment was measured after 30 min.

ABBREVIATIONS

ABC, ATP-binding cassette superfamily; BSEP, bile salt export pump; BSP, sulfobromophthalein; CDNB, 1-chloro-2,4-nitrobenzene, DHEAS, dehydroepiandrosterone 3-sulfate; DiOC6(3), 3,3'-dihexyloxacarbocyanine iodide; E$_2$17bG, 17b-glucuronosyl estradiol; Fluo-3,1-[2-amino-5-(2,7-dichloro-6-hydroxy-3-oxo-3H-xanthen-9-yl)]-2-(2'-amino-5'-methyl-phenoxy)-ethane-N,N,N',N'-tetraacetic acid penta-ammonium salt; HEK293, human embryonic kidney cells; HPLC, high-performance liquid chromatography; HSA, human serum albumin; $K_m$, Michaelis-Menten constant; LTC$_4$, leukotriene C$_4$; MDCKII, Madin-Darby canine kidney cells, strain II; MRP2, multidrug resistance protein 2; OAT1, organic anion transporter 1; OATP, human organic anion-transporting polypeptide; OCT1, organic cation transporter 1; SLC, solute carrier superfamily; TC, taurocholate or cholyl taurine; SDS, sodium dodecyl sulfate The present invention is explained by the examples.

EXAMPLE 1

Materials and Methods (A) Chemicals. [$^3$H]BSP (0.5 TBq/mmol) was obtained from Hartmann Analytic (Köln, Germany) by custom synthesis (Cui et al. 2001). [14,15,19,20-$^3$H]LTC$_4$, [1,2,6,7-$^3$H] dehydroepiandrosterone sulfate (0.6 TBq/mmol), [$^3$H] cholyl taurine (73 GBq/mmol), and 17b-D-glucuronosyl [6,7-$^3$H]estradiol (1.6 TBq/mmol) were purchased from Perkin-Elmer Life Science Products (Boston, Mass.). [$^{14}$C]Inulin carboxylic acid (82 MBq/g) was obtained from Biotrend Chemicals (Köln, Germany). Fluo-3 (1-[2-amino-5-(2,7-dichloro-6-hydroxy-3-oxo-3H-xanthen-9-yl)]-2-(2'-amino-5'-methyl-phenoxyl)-ethane-N,N,N',N'-tetraacetic acid penta-ammonium salt) was from Calbiochem (Bad Soden, Germany). Rifampicin, rifamycin SV, acivicin, and CDNB were purchased from Sigma (Deisenhofen, Germany). G418 (geneticin) sulfate was from Life Technologies (Gaithersburg, Md.). Hygromycin was from Invitrogen (Groningen, Netherlands). Additional non-radioactive chemicals of analytical purity were obtained from Sigma.

(B) Cell Culture and Transfection. HEK293 (human embryonic kidney) and MDCKII (strain II of Madin-Darby canine kidney) cells were cultured in minimum essential medium supplemented with 10% fetal bovine serum, 100 U/ml penicillin, and 100 μg/ml streptomycin at 37° C., 95% humidity, and 5% CO$_2$. HEK-MRP2 and HEK-Co are HEK293 cells transfected with human MRP2 cDNA and control vector, respectively; MDCK-MRP2 and MDCK-Co are MDCKII cells transfected with human MRP2 cDNA and control vector, respectively, as described (Cui et al. 1999).

The human OATP8 cDNA (König et al. 2000b) was subcloned into the mammalian expression vector pcDNA3.1/Hygro(+) (Invitrogen) and transfected into MDCKII cells using the polybrene method (König et al. 2000b). Transfectants expressing recombinant OATP8 were selected with hygromycin (950 μM). The clone with the highest OATP8 expression (MDCK-OATP8) was further transfected with the vector construct pcDNA3.1-MRP2 with the full-length human MRP2 cDNA (Cui et al. 1999). After selection with 950 μM hygromycin and 800 μM G418 disulfate for three weeks, the transfectants were screened for both MRP2 and OATP8 expression by immunoblot analyses. A clone with the highest MRP2 expression and a similar expression level of OATP8 as MDCK-OATP8 cells was designated as MDCK-MRP2/OATP8 and chosen for further studies.

(C) Immunoblot Analysis. Crude membrane fractions were prepared from cultured MDCKII cells as described earlier (Cui et al. 1999). Proteins were separated by SDS-PAGE (7.5% gels). OATP8 was detected by the polyclonal antibody SKT (König et al. 2000b) at a dilution of 1:5000 in TBS-T (20 mM Tris, 145 mM NaCl, 0.05% Tween 20, pH 7.6). MRP2 was detected by the polyclonal antibody EAG5 (Büchler et al., 1996; Keppler and Kartenbeck, 1996) at a dilution of 1:10000 in TBS-T.

(D) Confocal Laser Scanning Immunofluorescence Microscopy. MDCKII cells were grown on Transwell membrane inserts (6.5 mm diameter, 0.4 μm pore size, Corning Costar, Bodenheim, Germany) for 3 days at confluency and induced with 10 mM sodium butyrate for 24 h (Cui et al. 1999). Cells were fixed with 2.5% paraformaldehyde in PBS (137 mM NaCl, 2.7 mM KCl, 8.0 mM Na$_2$HPO$_4$, 1.5 mM KH$_2$PO$_4$, pH 7.4) for 20 min, permeabilized with 1% Triton X-100 in PBS for 20 min, and incubated for 1.5 h with primary antibodies at room temperature. The polyclonal antibody SKT (König et al. 2000b), at a dilution of 1:25 in PBS, and the monoclonal mouse antibody M$_2$III-6 (Alexis Biochemicals, Grünberg, Germany) at a dilution of 1:20 in PBS, were used to stain OATP8 and MRP2, respectively. Cells were then washed three times with PBS and incubated with secondary antibodies. Both Cy2-conjugated goat anti-rabbit IgG and Cy3-conjugated goat anti-mouse IgG were obtained from Jackson Laboratories (West Grove, Pa.) and used at a dilution of 1:200 in PBS. The Transwell membranes were then cut from the membrane inserts and mounted using 50% glycerol in PBS onto the slides. Confocal laser scanning microscopy was performed with a LSM 510 apparatus from Zeiss (Oberkochen, Germany).

(E) Transport Assays. For transport assays MDCKII cells were grown on Transwell membrane inserts (24 mm diameter, 0.4 μm pore size, Corning Costar) at confluency for 3 days and induced with 10 mM sodium butyrate for 24 h. Cells were first washed with transport buffer (142 mM NaCl, 5 mM KCl, 1 mM KH$_2$PO$_4$, 1.2 mM MgSO$_4$, 1.5 mM CaCl$_2$, 5 mM glucose, and 12.5 mM HEPES, pH 7.3), subsequently, $^3$H-labeled substrates were added in transport buffer either to the apical compartments (1 ml) or to the basolateral compartments (1.5 ml). After the time periods indicated, the radioactivity in the opposite compartments was measured. The intracellular accumulation of the radioactivity was determined by lysing the cells with 2 ml 0.2% SDS in water and measuring the radioactivity in cell lysates.

To study the transcellular transport of Fluo-3, cells were incubated with 2 μM Fluo-3 in the basolateral compartments at 37° C. for 30 min. The fluorescence of Fluo-3 in the apical compartment was measured with a RF-510 fluorescence spectrometer (Shimadzu, Duisburg, Germany) at an excitation wave length of 506 nm (5 nm bandwidth) and an emission wavelength of 526 nm (10 nm bandwidth) in the presence of 1.5 mM Ca$^{2+}$ (Nies et al. 1998).

To study the transcellular transport of rifampicin, cells were incubated with 50 μM rifampicin in the basolateral compartments at 37° C. for 30 min. To determine the concentration of rifampicin in the apical compartments its absorption at 475 nm was measured with a spectrophotometer (Ultrospec III, Amersham-Pharmacia, Freiburg, Germany). A calibration curve for the calculation of the concentrations of rifampicin was determined in the concentration range between 1 and 50 μM.

For inhibition studies the inhibitors were added simultaneously with [$^3$H]BSP into the basolateral compartments, with the exception of 1-chloro-2,4-dinitrobenzene (CDNB). In this case, MDCKII cells grown on Transwell membrane inserts were pre-incubated with CDNB in transport puffer in both apical and basolateral compartments for 20 min at room temperature. The transcellular transport was then started by replacing the buffer in the basolateral compartments by fresh buffer containing CDNB and [$^3$H]BSP.

The transcellular leakage was determined by incubating cells with 50 μM [$^{14}$C]inulin carboxylic acid in the basolateral compartments for 30 min and measuring the radioactivity in the apical compartments. For all four MDCKII cell lines used in this work the transcellular leakage was lower than 1%.

HPLC Analysis of [$^3$H]BSP. MDCK-MRP2/OATP8 cells grown on Transwell membrane inserts were incubated with 1 µM [$^3$H]BSP in the basolateral compartment for 30 min at 37° C. after a pre-incubation with 5 mM acivicin, an inhibitor of g-glutamyltransferase (Allen et al. 1980), in both compartments for 30 min at 37° C. The radioactivity in the apical compartment and in the cell lysate was analyzed by HPLC. Reversed-phase HPLC analyses on a $C_{18}$ Hypersil column (5-mm particles; Shandon, Runcorn, UK) were performed as described (Cui et al. 2001) using a linear gradient elution from 100% buffer A (45% methanol/55% water containing 2 mm tetrabutylammonium hydroxide at pH 6.0) to 100% buffer B (90% methanol/10% water containing 2 mM tetrabutylammonium hydroxide at pH 6.0) at a flow rate of 1 ml/min. [$^3$H]BSP-SG was synthesized for the HPLC analyses by incubating 1 mM GSH, 0.4 mM [$^3$H]BSP (1 µCi), and 5 mM acivicin with 350 µl mouse liver cytosol in a final volume of 500 µl for 1 h at 37° C. After deproteinization with 3 volume of methanol 200 µl supernatant was analyzed by HPLC as described above.

Vesicle Transport Studies. Transport of [$^3$H]BSP into membrane vesicles was measured by the rapid filtration method (Keppler et al. 1998). Briefly, membrane vesicles (30 µg protein) were incubated in the presence of 4 mM ATP, 10 mM creatine phosphate, 100 µg/ml creatine kinase, and [$^3$H]BSP in an incubation buffer (250 mM sucrose, 10 mM Tris/HCl, pH 7.4) in a final volume of 55 µl at 37° C. Aliquots (15 µl) were taken at the indicated time points, diluted in 1 ml ice-cold incubation buffer, and immediately filtered through presoaked nitrocellulose membrane (0.2 µm pore size, Schleicher & Schüll, Dassel, Germany). Filters were rinsed twice with 5 ml of incubation buffer, dissolved in liquid scintillation fluid, and counted for radioactivity. In control experiments, ATP was replaced by an equal concentration of 5'-AMP. ATP-dependent transport was calculated by subtracting values obtained in the presence of 5'-AMP from those obtained in the presence of ATP.

EXAMPLE 2

Expression and Localization of Recombinant Human OATP8 and MRP2 in MDCKII Cells

Figure 1:
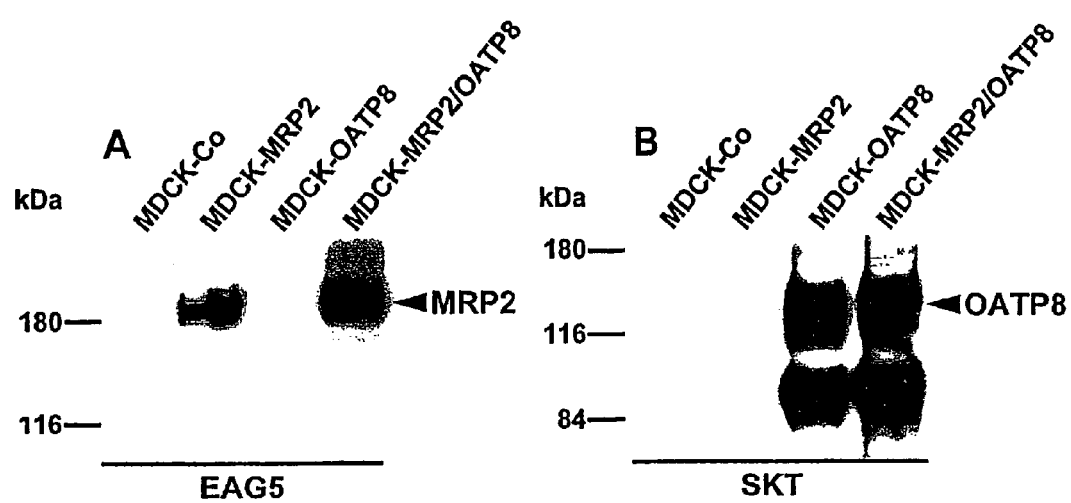
FIG. 1. Immunoblot analysis of MRP2 and OATP8 in transfected MDCK cells. Crude membrane fractions from MDCK cells permanently transfected with control vector (MDCK-Co), with human MRP2 (MDCK-MRP2), with human OATP8 (MDCK-OATP8), or with both MRP2 and OATP8 cDNA (MDCK-MRP2/OATP8) were separated by SDS-PAGE. A, Human MRP2 was detected by the polyclonal antibody EAG5 (Keppler and Kartenbeck 1996; Schaub et al. 1999). B, Human OATP8 was detected by the polyclonal antibody SKT (König et al. 2000b). In case of OATP8, only the fully glycosylated form is indicated by an arrowhead, whereas the band at about 90 kDa represents an under-glycosylated form of the protein (König et al. 2000b).

The expression of human OATP8 and MRP2 in the transfected MDCKII cells was first analyzed by immunoblotting (FIG. 1). As shown in FIG. 1A, MRP2 expression was detected by the antibody EAG5 in MDCKII cells transfected with MRP2 cDNA alone (MDCK-MRP2) or with both OATP8 and MRP2 cDNA (MDCK-MRP2/OATP8). The expression of OATP8 was detected by the antibody SKT in MDCKII cells transfected with OATP8 cDNA alone (MDCK-OATP8) and in MDCK-MRP2/OATP8 cells (FIG. 1B). Consistent with our earlier report (König et al. 2000b), the fully glycosylated form of human OATP8 has an apparent molecular weight of about 120 kDa, the bands with lower apparent molecular weight detected by the antibody SKT resulted from the under-glycosylated forms of OATP8. In the MDCKII cells transfected with the control vector (MDCK-Co) neither expression of human OATP8 nor MRP2 could be detected (FIG. 1).

Figure 2:
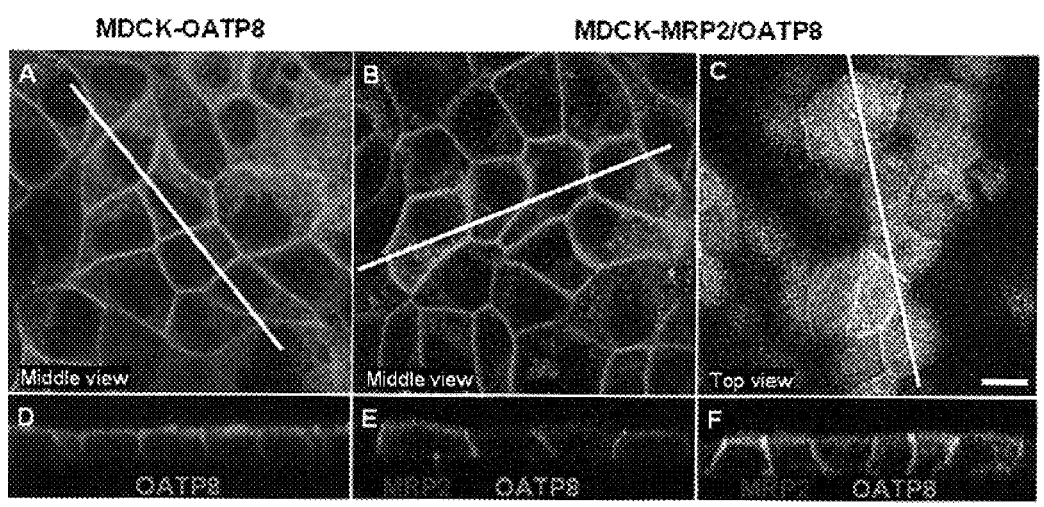
FIG. 2. Immunolocalization of recombinant MRP2 and OATP8 in MDCK cells. MDCK cells expressing OATP8 alone (A, D) or both MRP2 and OATP8 (B, C, E, and F) were grown on Transwell membrane inserts and examined by confocal laser scanning microscopy. OATP8 (green fluorescence) and MRP2 (red fluorescence) were stained using the polyclonal antibody SKT (König et al. 2000b) and the monoclonal antibody $M_2III_6$ (Evers et al. 1998), respectively. A and B are en face images focused at the middle of the cell monolayer, C is an en face image focused at the top of the cell monolayer. D, E, and F are vertical sections at the positions indicated by the white lines in A, B, and C. Besides the lateral localization of OATP8, some intracellular staining of this protein can be seen in the vertical sections. Only MRP2 is localized to the apical membrane (E, F). Bar, 10 μm.
Figure 3:
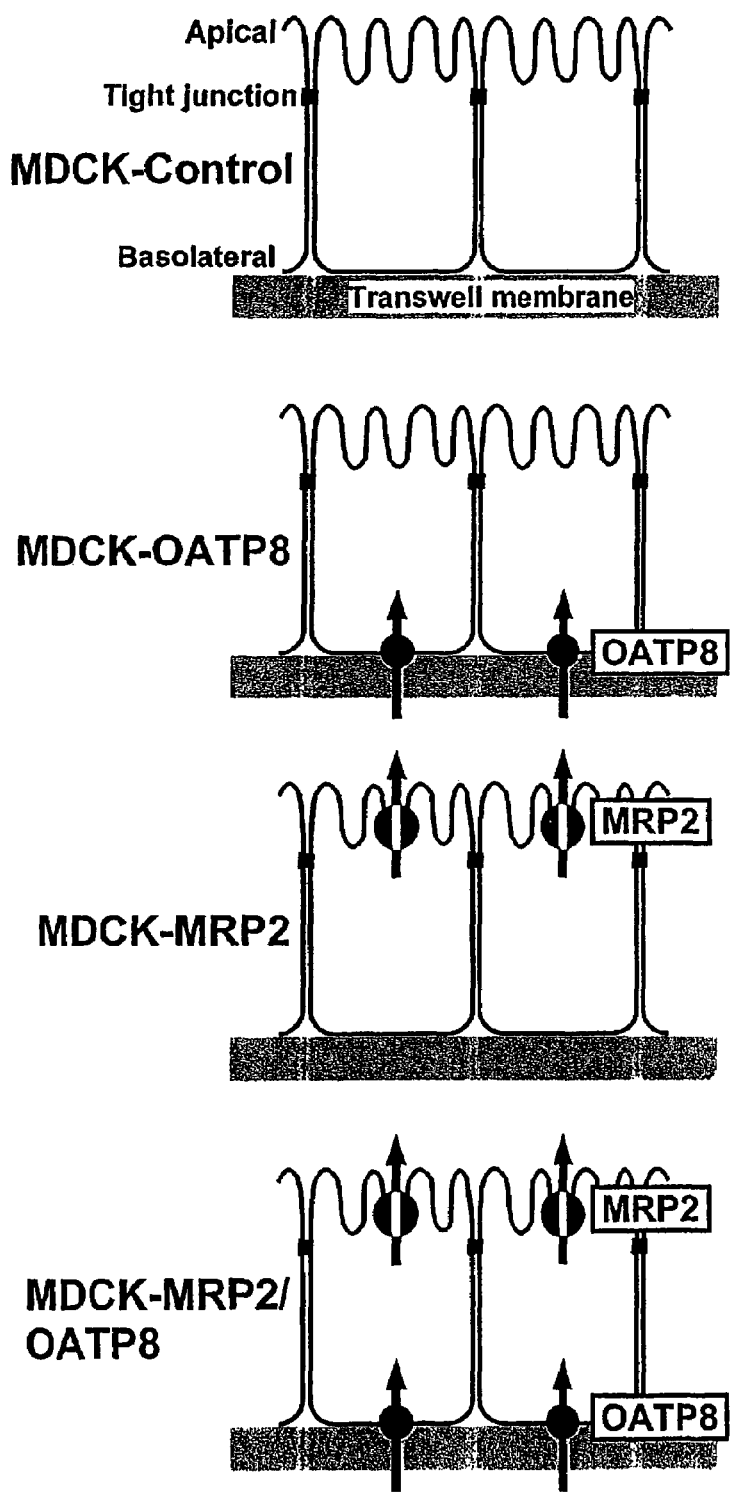
FIG. 3. Scheme of the MDCK transfectants growing on the Transwell membrane inserts as a polarized monolayer. The apical membrane facing the culture medium is separated from the basolateral membrane facing the membrane support by the tight junctions. The export pump MRP2 is localized to the apical membrane, whereas the uptake transporter OATP8 is localized to the basolateral membrane.

The cellular localization of the recombinant transporters in the transfectants was studied by means of immunofluorescence and confocal laser scanning microscopy. In MDCK-OATP8 cells, OATP8 could be stained with the antibody SKT in the basolateral membrane (FIGS. 2A and D). In these cells, also some intracellular staining of OATP8 was observed. Double-labeling experiments using the antibody SKT and $DiOC_6(3)$ which stains specifically the endoplasmic reticulum (Terasaki et al. 1984) indicated that the intracellular OATP8 fraction was localized to the ER (not shown). The partial ER localization of OATP8 corresponds to its biogenesis and is consistent with the existence of under-glycosylated OATP8 observed in immunoblot analyses (FIG. 1B). In MDCK-MRP2/OATP8 cells, MRP2 was localized to the apical membrane, in addition to the lateral appearance of OATP8 (FIGS. 2B, C, E, and F). FIG. 2B shows an image focused in the plane of the nuclei where only OATP8 was visible in this plane. FIG. 2C shows an image focused at the top of the cells, where the MRP2 staining could be seen. In vertical sections both OATP8 and MRP2 were visible (FIGS. 2E and 2F). FIG. 3 shows schematically the role of both recombinant transporters in the vectorial transport by the respective transfected cell line.

EXAMPLE 3

Transcellular Transport of [$^3$H]BSP Mediated by OATP8 and MRP2

Figure 4:
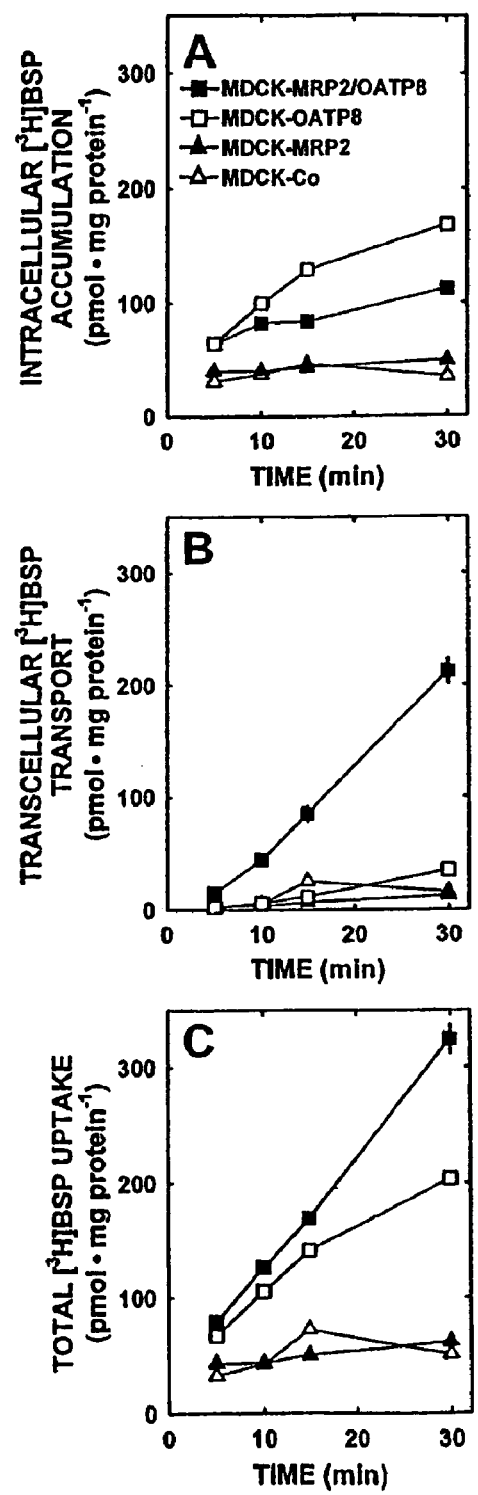
FIG. 4. Transcellular transport of [$^3$H]BSP. MDCK-Co (è), MDCK-MRP2 (s), MDCK-OATP8 (c), and MDCK-MRP2/OATP8 (g) cells were grown on Transwell membrane inserts. [$^3$H]BSP (1 μM) was given to the basolateral compartments. At the time points indicated, radioactivity in the apical compartments (Transcellular [$^3$H]BSP transport) and inside the cells (Intracellular [$^3$H]BSP accumulation) was determined. Total uptake of [$^3$H]BSP was calculated as the sum of intracellular and apical radioactivity. Data represent means±SD (n=4). For most measurements the standard deviation was within the size of the symbols.

The function of human OATP8 and MRP2 in the double-transfected cells was studied by measurement of the transcellular transport of the organic anion [3H]BSP, a substrate of human OATP8 (König et al. 2000b, Cui et al., 2001). Thus, polarized MDCKII cells grown on Transwell membrane inserts were incubated with [$^3$H]BSP at a concentration of 1 µM in the basolateral compartments. At different time points, the radioactivity accumulated in the apical compartment and in the cells was measured. As shown in FIG. 4A, the intracellular accumulation of [$^3$H]BSP was significantly higher in MDCKII cells transfected either with OATP8 cDNA alone (MDCK-OATP8) or with both OATP8 and MRP2 cDNA (MDCK-MRP2/OATP8) than in the control-transfected (MDCK-Co) and in the MRP2-transfected (MDCK-MRP2) cells, demonstrating that OATP8 is necessary for the intracellular accumulation of [$^3$H]BSP. However, when the radioactivity in the apical compartment was measured, no significant transfer of [$^3$H]BSP from the basolateral compartments into the apical compartments could be observed for MDCK-Co, MDCK-MRP2, and MDCK-OATP8 cells (FIG. 4B), whereas a marked transcellular transport of [$^3$H]BSP could be observed with MDCK-MRP2/OATP8 cells (FIG. 4B). FIG. 4C demonstrates a higher total uptake of [$^3$H]BSP (intracellular accumulation plus transcellular transport) by the MDCK-MRP2/OATP8 cells than by the MDCK-OATP8 cells.

Figure 5:
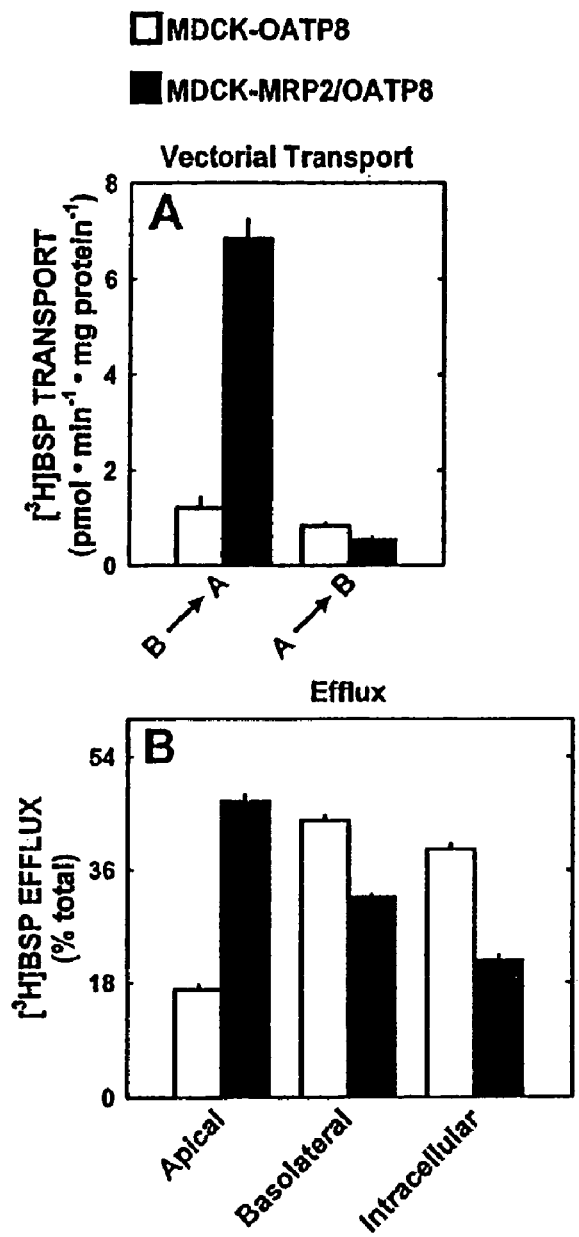
FIG. 5. Vectorial transport and efflux of [$^3$H]BSP. MDCK-OATP8 and MDCK-MRP2/OATP8 cells were grown on Transwell membrane inserts. A, Vectorial transport of [$^3$H] BSP. [$^3$H]BSP (1 μM) was given either to the basolateral compartments (B® A) or to the apical compartments (A® B). After 15 min at 37° C., radioactivity in the opposite compartments was measured. B, Efflux of [$^3$H]BSP. MDCK-OATP8 and MDCK-MRP2/OATP8 cells were incubated with [$^3$H]BSP (1 μM) in the basolateral compartments at 37° C. for 30 min. The cells were then washed with cold buffer and incubated with buffer without [$^3$H]BSP at 37° C. for 30 min. The radioactivity subsequently released into the basolateral and the apical compartment and inside the cells was measured. Data represent means ±SD (n=4).

The transcellular transport of [$^3$H]BSP by the MDCK-MRP2/OATP8 cells was a vectorial process, as shown in FIG. 5A. Only a basolateral to apical transport of [$^3$H]BSP was observed, whereas the apical to basolateral transport was negligible. This was expected from the cellular localization of OATP8 and MRP2 in the double-transfectants and from the unidirectionality of MRP2-mediated transport (FIG. 3).

The efflux of [$^3$H]BSP was determined after incubation of MDCK-OATP8 and MDCK-MRP2/OATP8 cells with 1 µM [$^3$H]BSP for 30 min in the basolateral compartment. As shown in FIG. 5B, [$^3$H]BSP was released from the MDCK-OATP8 cells mainly across the basolateral membrane, whereas it was exported from the MDCK-MRP2/OATP8 cells mainly across the apical membrane. When the radioactivity remaining in the cells after the 30 min efflux experiments was compared, the MDCK-MRP2/OATP8 cells showed a significantly lower intracellular [$^3$H]BSP level than the MDCK-OATP8 cells, indicating the efficient export via MRP2 in the apical membrane.

EXAMPLE 4

Figure 6:
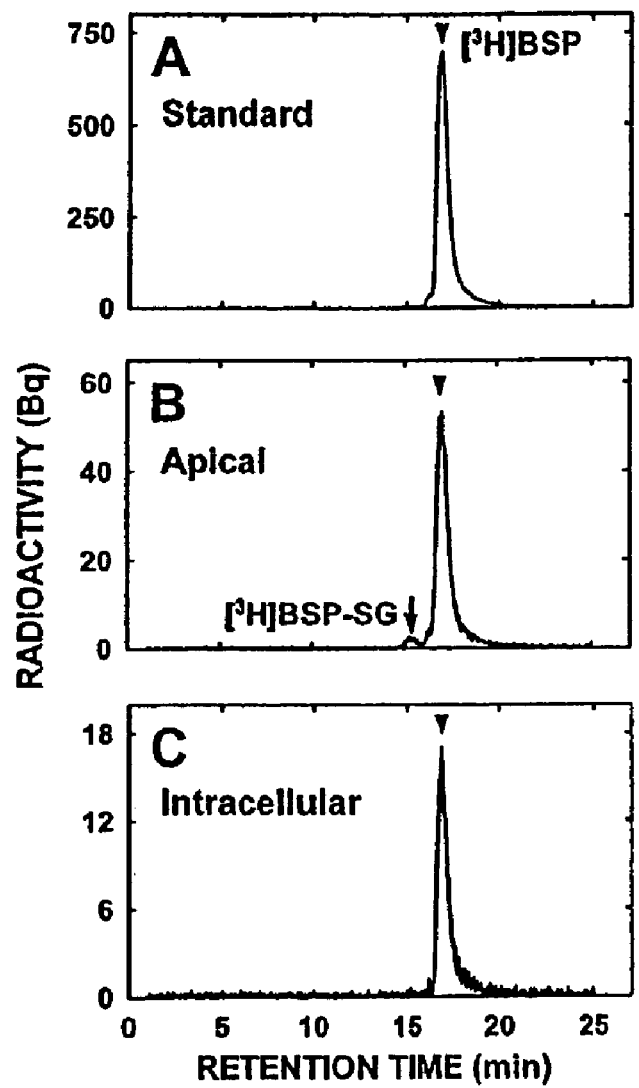
FIG. 6. HPLC analyses of [$^3$H]BSP. MDCK-MRP2/OATP8 cells grown on Transwell membrane inserts were incubated with 1 μM [$^3$H]BSP in the basolateral compartment at 37° C. for 30 min. The medium in the apical compartment and the cell lysate were analyzed by radio-HPLC as described in "Materials and Methods". A, Authentic [$^3$H]BSP (Cui et al. 2001); B, radioactivity collected in the apical compartment; C, radioactivity accumulated in the cells. [$^3$H]BSP (arrow head) and the glutathione S-conjugate of [$^3$H]BSP ([$^3$H]BSP-SG, arrow) are indicated. Acivicin, an inhibitor of the degradation of the glutathione moiety of [$^3$H]BSP-SG, was added to the incubation at a concentration of 5 mM.

BSP Itself and Not its Glutathione S-Conjugate is Transported by MRP2 in the Double-transfected MDCK Cells Studies in rat liver showed that BSP is secreted into bile mainly as glutathione conjugate (Combs 1965; Klaassen and Plaa 1967). To investigate whether this is also true for the double-transfectants, we checked the radioactivity in the apical compartment of the MDCK-MRP2/OATP8 cells by radio-HPLC after incubation of the cells with 1 μM [$^3$H]BSP in the basolateral compartment for 30 min. The majority of the radioactivity (>98%) that was accumulated in the apical compartment (FIG. 6B) and in the cells (FIG. 6C) showed the same retention time (17 min) as the unconjugated [$^3$H]BSP (FIG. 6A). Only a small peak of [$^3$H]BSP-SG (retention time 15 min) was observed in the apical compartment (FIG. 6B). These results suggest that BSP is taken up by human OATP8 and is itself, rather than its glutathione S-conjugate, a substrate for MRP2 during transcellular transport. To confirm this hypothesis we investigated the transport of [3H]BSP into inside-out membrane vesicles prepared from HEK-MRP2 cells (HEK293 cells transfected with human MRP2, Cui et al. 1999). As shown in FIG. 7A, [$^3$H]BSP was transported ATP-dependently into membrane vesicles from HEK-MRP2 cells. The accumulation of [$^3$H]BSP in the membrane vesicles from HEK-MRP2 cells was significantly higher than in the membrane vesicles from control-transfected HEK-Co cells (FIG. 7B) demonstrating that [$^3$H]BSP is a substrate for human MRP2. A $K_m$ value of 12 μM for BSP was determined for MRP2 (FIG. 7C).

EXAMPLE 5

Transcellular Transport of Other Organic Anions

Transcellular transport of other organic anions which are substrates for both OATP8 and MRP2 was also studied. [$^3$H]Leukotriene $C_4$ (LTC$_4$), 17b-glucuronosyl [H]estradiol (E$_2$17bG), and [$^3$H]dehydroepiandrosterone sulfate (DHEAS) have already been identified as OATP8 substrates (König et al. 2000b; Kullak-Ublick et al. 2001; Cui et al. 2001). [$^3$H]LTC$_4$ and [$^3$H]E$_2$17bG have been shown to be high affinity substrates for MRP2 (Cui et al. 1999). Our studies also identified [$^3$H]DHEAS as a substrate of MRP2 (Gologan, Leier, and Keppler, unpublished data, 2001). Similar to [$^3$H]BSP (FIG. 8A), all three compounds were transported with much higher velocities across MDCK-MRP2/OATP8 cells than across MDCK-OATP8 or MDCK-Co cells (FIG. 8B, C, D). Fluo-3 is a fluorescent compound (Minta et al. 1989) and a good substrate for MRP2 (Nies et al. 1998). Like the other compounds mentioned above, Fluo-3 was transported across the MDCK-MRP2/OATP8 cell monolayer with a higher transport rate in comparison to the MDCK-OATP8 cell monolayer (FIG. 8E), suggesting that Fluo-3 is also a substrate for human OATP8.

In FIG. 8F the transcellular transport of [$^3$H]cholyl taurine (TC), which is neither a substrate for human OATP8 (König et al. 2000b, Cui et al. 2001) nor for MRP2 (Madon et al. 1997), was studied. Unlike the other compounds tested, [$^3$H]cholyl taurine was transported across all three MDCKII cell lines with a quite high velocity, but no difference in transport rates was observed between MDCK-Co, MDCK-OATP8, and MDCK-MRP2/OATP8 cells. The high transport rate for [$^3$H]cholyl taurine by the MDCK cells is probably a result of the expression of endogenous transport systems for bile salts.

EXAMPLE 6

Inhibition of Transcellular [$^3$H]BSP Transport

The hydrophobic compound CDNB which is thought to enter cells via diffusion is conjugated with glutathione inside the cell and then pumped out via MRP2 (Evers et al. 1998). These properties of CDNB allowed us to differentiate between the uptake mediated by OATP8 and the export mediated by MRP2. Transfected MDCK cells were pre-incubated with different concentrations of CDNB at room temperature for 20 min before measurement of the transcellular [$^3$H]BSP transport. As shown in FIG. 9A, the intracellular accumulation and the transcellular transport of [$^3$H]BSP in MDCK-OATP8 cells was not inhibited by CDNB up to a concentration of 50 μM. However, CDNB exerted a completely different effect on MDCK-MRP2/OATP8 cells. The intracellular accumulation of [$^3$H]BSP was enhanced, whereas the transcellular transport of [$^3$H]BSP was markedly inhibited by the pre-incubation with CDNB (FIG. 9B). These results indicate that CDNB does not affect the OATP8-mediated uptake, but inhibits the MRP2-mediated export of [$^3$H]BSP after formation of dinitrophenylglutathione inside the cells.

We have recently reported that human serum albumin (HSA) potently inhibits OATP8-mediated uptake of [$^3$H] BSP, probably by binding [$^3$H]BSP with very high affinity (Cui et al. 2001). Thus, we studied here the effect of HSA on the transcellular transport of [$^3$H]BSP across the MDCKII transfectants. In the presence of 5 μM HSA the OATP8-mediated accumulation of [$^3$H]BSP in MDCK-OATP8 cells was suppressed almost completely (FIG. 9C). Also in the MDCK-MRP2/OATP8 cells, the [$^3$H]BSP accumulation was strongly inhibited by HSA (FIG. 9D). Consequently, the transcellular transport of [$^3$H]BSP was also diminished in the MDCK-MRP2/OATP8 cells (FIG. 9D).

OATP8-mediated uptake of [$^3$H]E$_2$17bG into OATP8-transfected HEK293 cells can be inhibited by the antibiotics rifampicin and rifamycin SV (Cui et al. 2001). FIG. 9E-H demonstrate that both antibiotics interfere strongly with both OATP8 and MRP2. Consistent with our earlier studies (Cui et al. 2001), both antibiotics inhibited the intracellular accumulation of [$^3$H]BSP in the MDCK-OATP8 cells (FIGS. 9E and G). In the MDCK-MRP2/OATP8 cells however, the intracellular accumulation of [$^3$H]BSP was only suppressed to about 50% of control, whereas the transcellular transport of [$^3$H]BSP was inhibited more strongly by rifampicin and rifamycin SV (FIGS. 9G and H). These results suggest that both compounds inhibit MRP2-mediated export in addition. This is confirmed by transport studies using membrane vesicles from HEK-MRP2 cells. Rifampicin at a concentration of 50 μM inhibited [$^3$H]LTC$_4$ transport into HEK-MRP2 membrane vesicles to 50% of control, and 50 μM rifamycin SV inhibited LTC$_4$ transport into HEK-MRP2 membrane vesicles to 38% of control.

EXAMPLE 7

Transcellular Transport of Rifampicin

Because rifampicin strongly inhibits both human OATP8 and MRP2, we were interested in whether the transcellular transport of rifampicin itself can be measured using our double-transfectants. We took the advantage of the intensive absorption of rifampicin at 475 nm to determine its concentration. A rifampicin concentration of as low as 1 µM could be measured by this method. As shown in FIG. 10, a significantly higher transcellular transport of rifampicin could be observed with MDCK-MRP2/OATP8 cells in comparison to the other three MDCKII transfectant cell lines. A rifampicin concentration of about 50 µm in these experiments was the lowest one that we could use to obtain rifampicin transport into the apical compartments in an amount detectable by the photometric method.

EXAMPLE 8

Additional Double-transfected Cell Lines

In addition to the above described double-transfected cell line MDCK-MRP2/OATP8 two further double transfected cell lines have been generated in the same manner: MDCK-OAT1/MRP2 and MDCK-OATP2/MRP2. The combination of the basolateral organic anion transporter OAT1 (gene symbol: SLC22A6; Hosoyomada et al, 1999) and the apical export pump MRP2 represents a model system for studies on renal transport processes. The combination of the basolateral organic anion transporter OATP2 (Abe et al., 1999; Hsiang et al, 1999; König et al., 2000a) and the apical export pump MRP2 represents a model system for studies on hepatic transport processes. The correct localisation of the recombinant transport proteins in the double-transfected cell lines was demonstrated by immunofluorescence confocal laser scanning microscopy (FIG. 11).

EXAMPLE 9

Transcellular Transport of Para-aminohippurate

The transport activity of the double-transfected cell line MDCK-OAT1/MRP2 was studied by the use of the widely used model compound para-aminohippurate (PAH). PAH has been used for studies on renal secretion of organic anions. In the renal proximal tubule epithelia, PAH is taken up from the blood at the basolateral membrane by OAT1 (Hosoyamada et al., 1999). Subsequently, PAH is secreted ATP-dependently by MRP2 (Leier et al, 1999) into the urine. As demonstrated in FIG. 12, the rate of transcellular transport of PAH is significantly higher in the double-transfected cell line MDCK-OAT1/MRP2 than in the control-transfected cell line MDCK-Co and in the single-transfected cell line MDCK-OAT1.

EXAMPLE 10

Transcellular Transport of BSP

The transport activity of the double-transfected cell line MDCK-OATP2/MRP2 was studied by the use of the model compound BSP. As demonstrated in FIG. 13, the rate of transcellular transport of BSP is significantly higher in the double-transfected cell line MDCK-OATP2/MRP2 than in the control-transfected cell line MDCK-Co and in the single-transfected cell line MDCK-OATP2.

BIBLIOGRAPHY

Abe T, Kakyo M, Tokui T, Nakagomi R, Nishio T. Nakai D, Nomura H, Unno M, Suzuki M, Naitoh T, Matsuno S and Yawo H (1999) Identification of a novel gene family encoding human liver-specific organic anion transporter LST-1. *J Biol Chem* 274:17159–17163.

Acocella G (1978) Clinical pharmacokinetics of rifampicin. *Clin Pharmacokinet* 3:108–127.

Allen L, Meck R and Yunis A (1980) The inhibition of gamma-glutamyl transpeptidase from human pancreatic carcinoma cells by (alpha S,5S)-alpha-amino-3-chloro-4, 5-dihydro-5-isoxazoleacetic acid (AT-125; NSC-163501). *Res Commun Chem Pathol Pharmacol* 27:175–182.

Borst P, Evers R, Kool M and Wijnholds J (2000) A family of drug transporters: the multidrug resistance-associated proteins. *J Natl Cancer Inst* 92:1295–1302.

Büchler M, König J, Brom M, Kartenbeck J, Spring H, Horie T and Keppler D (1996) cDNA cloning of the hepatocyte canalicular isoform of the multidrug resistance protein, cMrp, reveals a novel conjugate export pump deficient in hyperbilirubinemic mutant rats. *J Biol Chem* 271:15091–15098.

Combes B (1965) The importance of conjugation with glutathione for sulfobromophthalein sodium (BSP) transfer from blood to bile. *J Clin Invest* 44: 1214–1222.

Cui Y, König J, Buchholz J K, Spring H, Leier I and Keppler D (1999) Drug resistance and ATP-dependent conjugate transport mediated by the apical multidrug resistance protein, MRP2, permanently expressed in human and canine cells. *Mol Pharmacol* 55:929–937.

Cui Y, König J, Leier I, Buchholz U and Keppler D (2001) Hepatic Uptake of Bilirubin and Its Conjugates by the Human Organic Anion Transporter SLC21A6. *J Biol Chem* 276:9626–9630.

Evers R, Kool M, van Deemter L, Janssen H, Calafat J, Oomen L C, Paulusma C C, Oude Elferink R P, Baas F, Schinkel A H, and Borst P (1998) Drug export activity of the human canalicular multispecific organic anion transporter in polarized kidney MDCK cells expressing cMOAT (MRP2) cDNA. *J Clin Invest* 101:1310–1319.

Gerloff T, Stieger B, Hagenbuch B, Madon J, Landmann L, Roth J, Hofmann A F and Meier P J (1998) The sister of P-glycoprotein represents the canalicular bile salt export pump of mammalian liver. *J Biol Chem* 273:10046–10050.

Hori R, Okamura M, Takayama A, Hirozane K and Takano M (1993) Transport of organic anion in the OK kidney epithelial cell line. *Am J Physiol* 264:F975–980.

Hosoyamada M, Sekine T, Kanai Y and Endou H (1999) Molecular cloning and functional expression of a multispecific organic anion transporter from human kidney. *Am J Physiol* 276:F122–128.

Hsiang B, Zhu Y, Wang Z, Wu Y, Sasseville V, Yang W P and Kirchgessner T G (1999) A novel human hepatic organic anion transporting polypeptide (OATP2). Identification of a liver-specific human organic anion transporting polypeptide and identification of rat and human hydroxymethylglutaryl-CoA reductase inhibitor transporters. J Biol Chem 274:37161–37168.

Ishizuka H, Konno K, Shiina T, Naganuma H, Nishimura K, Ito K, Suzuki H and Sugiyama Y (1999) Species differences in the transport activity for organic anions across the bile canalicular membrane. *J Pharmacol Exp Ther* 290:1324–1330.

Ito K, Suzuki H, Hirohashi T, Kume K, Shimizu T and Sugiyama Y (1997) Molecular cloning of canalicular multispecific organic anion transporter defective in EHBR. *Am J Physiol* 272:G16–22.

Ito K, Suzuki H, Hirohashi T, Kume K, Shimizu T and Sugiyama Y (1998) Functional analysis of a canalicular multispecific organic anion transporter cloned from rat liver. *J Biol Chem* 273:1684–1688.

Jansen P L (2000) Foreword: from classic bile physiology to cloned transporters. *Semin Liver Dis* 2000 20:245–250.

Jansen P L, Groothuis G M, Peters W H and Meijer D F (1987) Selective hepatobiliary transport defect for organic anions and neutral steroids in mutant rats with hereditary-conjugated hyperbilirubinemia. *Hepatology* 7:71–76.

Keppler D and Arias I M (1997) Hepatic canalicular membrane. Introduction: transport across the hepatocyte canalicular membrane. *FASEB J* 11:15–18.

Keppler D, Jedlitschky G and Leier I (1998) Transport function and substrate specificity of multidrug resistance protein. *Methods Enzymol* 292:607–616.

Keppler D and Kartenbeck J (1996) The canalicular conjugate export pump encoded by the cmrp/cmoat gene. *Prog Liver Dis* 14:55–67.

Klaassen C D and Plaa G L. (1967) Species variation in metabolism, storage and excretion of sulfobromophthalein. *Am J Physiol* 213:1322–1326.

König J, Cui Y, Nies A T and Keppler D (2000a) A novel human organic anion transporting polypeptide localized to the basolateral hepatocyte membrane. *Am J Physiol Gastrointest Liver Physiol* 278:G156-G164.

König J, Cui Y, Nies A T and Keppler D (2000b) Localization and genomic organization of a new hepatocellular organic anion transporting polypeptide. *J Biol Chem* 275:23161–23168.

König J, Nies A T, Cui Y, Leier I and Keppler D (1999) Conjugate export pumps of the multidrug resistance protein (MRP) family: localization, substrate specificity, and MRP2-mediated drug resistance. *Biochim Biophys Acta* 1461:377–394.

Kullak-Ublick G A, Stieger B, Hagenbuch B and Meier P J (2000) Hepatic transport of bile salts. *Semin Liver Dis* 20:273–293.

Kullak-Ublick G A, Ismair M G, Stieger B, Landmann L, Huber R, Pizzagalli F, Fattinger K, Meier P J and Hagenbuch B (2001) Organic anion-transporting polypeptide B (OATP-B) and its functional comparison with three other OATPs of human liver. *Gastroenterology* 120:525–533.

Leier I., Hummel-Eisenbeiss J., Cui Y, Keppler D. (2000), ATP-dependent para-aminohippurate transport by apical multidrug resistance protein MRP2, Kidney Int. 57: 1636–1642

Li L, Lee T K, Meier P J and Ballatori N (1998) Identification of glutathione as a driving force and leukotriene C4 as a substrate for oatp1, the hepatic sinusoidal organic solute transporter. *J Biol Chem* 273:16184–16191.

Madon J, Eckhardt U, Gerloff T, Stieger B and Meier P J (1997) Functional expression of the rat liver canalicular isoform of the multidrug resistance-associated protein. *FEBS Lett* 406:75–78.

Minta A, Kao J P and Tsien R Y (1989) Fluorescent indicators for cytosolic calcium based on rhodamine and fluorescein chromophores. *J Biol Chem* 264:8171–8178.

Nies A T, Cantz T, Brom M, Leier I and Keppler D (1998) Expression of the apical conjugate export pump, Mrp2, in the polarized hepatoma cell line, WIF-B. *Hepatology* 28:1332–1340.

Paulusma C C, Bosma P J, Zaman G J, Bakker C T, Otter M, Scheffer G L, Scheper R J, Borst P and Oude Elferink R P (1996) Congenital jaundice in rats with a mutation in a multidrug resistance-associated protein gene. *Science* 271:1126–1128.

Scharschmidt B F, Waggoner J G and Berk P D (1975) Hepatic organic anion uptake in the rat. *J Clin Invest* 56:1280–1292.

Schaub T P, Kartenbeck J, König J, Spring H, Dorsam J, Staehler G, Störkel S, Thon W F and Keppler D (1999) Expression of the MRP2 gene-encoded conjugate export pump in human kidney proximal tubules and in renal cell carcinoma. *J Am Soc Nephrol* 10:1159–1169.

Snel C A, Pang K S and Mulder G J (1995) Glutathione conjugation of bromosulfophthalein in relation to hepatic glutathione content in the rat in vivo and in the perfused rat liver. *Hepatology* 21:1387–1394.

Strautnieks S S, Bull L N, Knisely A S, Kocoshis S A, Dahl N, Arnell H, Sokal E, Dahan K, Childs S, Ling V, Tanner M S, Kagalwalla A F, Nemeth A, Pawlowska J, Baker A, Mieli-Vergani G, Freimer N B, Gardiner R M and Thompson R J (1998) A gene encoding a liver-specific ABC transporter is mutated in progressive familial intrahepatic cholestasis. *Nat Genet* 20:233–238.

Suzuki H and Sugiyama Y (1998) Excretion of GSSG and glutathione conjugates mediated by MRP1 and cMOAT/MRP2. *Semin Liver Dis* 18:359–376.

Terasaki M, Song J, Wong J R, Weiss M J and Chen L B (1984) Localization of endoplasmic reticulum in living and glutaraldehyde-fixed cells with fluorescent dyes. *Cell* 38:101–108.

Tojo A, Sekine T, Nakajima N, Hosoyamada M, Kanai Y, Kimura K and Endou H (1999) Immunohistochemical localization of multispecific renal organic anion transporter 1 in rat kidney. *J Am Soc Nephrol* 10:464–471.

Wang R, Salem M, Yousef I M, Tuchweber B, Lam P, Childs S J, Helgason C D, Ackerley C, Phillips M J and Ling V (2001) Targeted inactivation of sister of P-glycoprotein gene (spgp) in mice results in nonprogressive but persistent intrahepatic cholestasis. *Proc Natl Acad Sci USA* 98:2011–2016.

Whelan G, Hoch J and Combes B (1970) A direct assessment of the importance of conjugation for biliary transport of sulfobromophthalein sodium. J Lab and Clin Med 75:542–557.

All publications, patents, and patent documents, cited in this application, are incorporated by reference herein, as though individually incorporated by reference. In the case of any inconsistencies, the present disclosure, including any definitions therein will prevail.

The invention has been described with reference to various specific and preferred embodiments and techniques.

However, it should be understood that many variations and modifications may be made while remaining within the spirit and scope of the invention.

The invention claimed is:

1. A polarized cell line double-transfected with (a) a DNA sequence encoding an uptake transporter for organic anions operatively linked with a promoter and (b) a DNA sequence encoding an export pump for organic anions or anionic conjugates operatively linked with a promoter, wherein the uptake transporter is a member of the subgroup 21A or 22A of the solute carrier (SLC) superfamily and the export pump is a member of the multidrug resistance transporter (MDR; ABCB) subgroup or the multidrug resistance protein (MRP; ABCC) subgroup of the ABC superfamily.

2. The cell line of claim 1 which is a canine or human cell line and the DNA sequences of (a) and/or (b) are human.

3. The cell line of claim 1 which is a kidney cell line.

4. The cell line of claim 1, wherein the uptake transporter for organic anions is OAT1 (SLC22A6), OATP2 (SLC21A6), OATP8 (SLC21A8) or OATP-B (SLC21A9).

5. The cell line of claim 1, wherein the export pump for organic anions or anionic conjugates is the bile salt export pump (BSEP; ABCB11) or the multidrug resistance protein 2 (MRP2; ABCC2).

6. The cell line of claim 1 wherein the DNA sequence encoding an uptake transporter for organic anions and/or the DNA sequence encoding an export pump for organic anions or anionic conjugates are operatively linked with a human cytomegalovirus immediate early promoter.

7. A method for identifying whether a candidate agent is a transport inhibitor comprising:
   (i) growing the cell line of claim 1 as a polarized monolayer having an apical and a basolateral compartment;
   (ii) incubating the cells with a transport buffer comprising a candidate agent and a labeled or fluorescent substrate in the apical or basolateral compartment; and
   (iii) measuring the labeled or fluorescent substrate in an apical or basolateral compartment opposite to the compartment of (ii) to determine whether the candidate agent inhibits cellular transport by the transporter for organic anions or the export pump for organic anions or anionic conjugates.

8. A method for identifying whether a candidate agent is a transport substrate comprising:
   (i) growing the cell line of claim 1 as a polarized monolayer having an apical and a basolateral compartment;
   (ii) incubating the cells with a candidate agent in the apical or basolateral compartment; and
   (iii) determining whether the candidate agent is transported by the transporter for organic anions or the export pump for organic anions or anionic conjugates by measuring the candidate agent in an apical or basolateral compartment opposite to the compartment of (ii).

9. The method of claim 7 wherein the candidate agent is a drug candidate.

10. The method of claim 7 or 8 wherein the identification of a transport substrate or a transport inhibitor is carried out as high throughput screening.

* * * * *